US006258550B1

(12) United States Patent
Evans et al.

(10) Patent No.: US 6,258,550 B1
(45) Date of Patent: Jul. 10, 2001

(54) POLYPEPTIDES THAT INCLUDE CONFORMATION-CONSTRAINING GROUPS WHICH FLANK A PROTEIN-PROTEIN INTERACTION SITE

(75) Inventors: Herbert J. Evans, Richmond, VA (US); R. Manjunatha Kini, Singapore (SG)

(73) Assignee: Virginia Commonwealth University, Richmond, VA (US)

(*) Notice: Subject to any disclaimer, the term of this patent is extended or adjusted under 35 U.S.C. 154(b) by 0 days.

(21) Appl. No.: 09/413,492

(22) Filed: Oct. 6, 1999

Related U.S. Application Data

(62) Division of application No. 08/934,224, filed on Sep. 19, 1997, which is a division of application No. 08/532,818, filed as application No. PCT/US94/04294 on Apr. 21, 1994, now Pat. No. 5,965,698, which is a continuation-in-part of application No. 08/051,741, filed on Apr. 23, 1993, now abandoned, and a continuation-in-part of application No. 08/143,364, filed on Oct. 29, 1993, now abandoned.

(51) Int. Cl.[7] .................................................. G01N 33/53
(52) U.S. Cl. ............................ 435/7.1; 435/183; 530/300
(58) Field of Search ...................................... 435/7.1, 183

(56) References Cited

U.S. PATENT DOCUMENTS

| | | | |
|---|---|---|---|
| 4,199,499 | 4/1980 | Smithwick et al. | 260/112.5 R |
| 4,215,111 | 7/1980 | Goldstein et al. | 424/177 |
| 4,251,439 | 2/1981 | Gesellchen et al. | 260/112.5 R |
| 4,261,886 | 4/1981 | Goldstein et al. | 260/112.5 R |
| 4,265,808 | 5/1981 | Gesellchen et al. | 260/112.5 R |
| 4,283,329 | 8/1981 | Gesellchen et al. | 260/112.5 R |
| 4,283,330 | 8/1981 | Shuman | 260/112.5 R |
| 4,309,343 | 1/1982 | Gesellchen et al. | 260/112.5 E |
| 4,316,890 | 2/1982 | Kamber et al. | 424/177 |
| 4,322,339 | 3/1982 | Gesellchen et al. | 260/112.5 E |
| 4,322,340 | 3/1982 | Shuman | 260/112.5 E |
| 4,333,873 | 6/1982 | Shuman | 260/112.5 E |
| 4,347,242 | 8/1982 | Neher et al. | 424/177 |
| 4,387,049 | 6/1983 | Pfeiffer | 260/112.5 R |
| 4,397,842 | 8/1983 | Goldstein et al. | 424/177 |
| 4,426,324 | 1/1984 | Meienhofer | 260/112.5 R |
| 4,448,717 | 5/1984 | Shuman | 260/112.5 E |
| 4,448,972 | 5/1984 | Pfeiffer | 548/528 |
| 4,473,497 | 9/1984 | Gesellchen et al. | 260/112.5 E |
| 4,505,853 | 3/1985 | Goldstein et al. | 260/112.5 R |
| 4,510,082 | 4/1985 | Gesellchen et al. | 260/112.5 R |
| 4,540,682 | 9/1985 | Hardy et al. | 514/18 |
| 4,558,033 | 12/1985 | Rudman | 514/4 |
| 4,629,723 | 12/1986 | Goldstein et al. | 514/17 |
| 4,699,897 | 10/1987 | Jones et al. | 514/4 |
| 4,783,442 | 11/1988 | Audhya et al. | 514/18 |
| 4,808,701 | 2/1989 | Danho et al. | 530/317 |
| 4,845,080 | 7/1989 | Fischer | 514/21 |
| 4,866,121 | 9/1989 | Audhya et al. | 525/54.1 |
| 5,019,647 | 5/1991 | Riemen et al. | 530/329 |
| 5,028,692 | 7/1991 | Oliff et al. | 530/329 |
| 5,047,502 | 9/1991 | Oliff et al. | 530/329 |
| 5,079,228 | 1/1992 | Cohen et al. | 514/12 |
| 5,128,448 | 7/1992 | Danho et al. | 530/329 |
| 5,182,263 | 1/1993 | Danho et al. | 514/16 |
| 5,227,469 | * 7/1993 | Lazarus | 530/324 |
| 5,268,358 | 12/1993 | Fretto | 514/12 |
| 5,350,836 | 9/1994 | Kopchick et al. | 530/399 |
| 5,451,399 | 9/1995 | Gimbrone et al. | 424/85.2 |
| 5,665,346 | 9/1997 | Clark-Lewis et al. | 424/85.2 |
| 5,702,919 | 12/1997 | Nash et al. | 435/69.5 |
| 5,840,524 | 11/1998 | Van Damme et al. | 435/69.1 |
| 5,928,896 | 7/1999 | Evans et al. | 435/69.1 |
| 5,948,887 | 9/1999 | Evans et al. | 530/333 |
| 5,952,465 | 9/1999 | Evans et al. | 530/333 |
| 5,965,698 | 10/1999 | Evans et al. | 530/326 |
| 6,084,066 | 7/2000 | Evans et al. | 530/333 |
| 6,100,044 | 8/2000 | Evans et al. | 435/7.1 |
| 6,111,069 | 8/2000 | Evans et al. | 530/333 |

FOREIGN PATENT DOCUMENTS

| | | |
|---|---|---|
| 2101919 | 8/1992 | (CA) . |
| 0256424A1 | 2/1988 | (EP) . |
| 0368486 | 5/1990 | (EP) . |
| 0399816A1 | 5/1990 | (EP) . |
| 0506477A1 | 3/1992 | (EP) . |
| WO89/05150 | 6/1989 | (WO) . |
| WO91/11458 | 8/1991 | (WO) . |
| WO 93/07169 | 4/1993 | (WO) . |

OTHER PUBLICATIONS

Scarborough, R. et al. J. Biol. Chem., 268:1058–1065, Jan. 1993.*
Audhya et al. Life Sci. 48(8): 773–780 (Abstract).
Hobbs et al. Clinical Immunology and Immunopathology 50: 251–263 (1989).
Abe et al. Eur. J. Biochem. 209: 933–937 (1992).
Kondo et al. Gene 81: 259–265 (1989).
Bernstein et al. Nature 340(6233): 482–486 (1989).
Chen et al. Proc. Natl. Acad. Sci. USA 89: 5872–5876 (1992).
Hruby et al. Synthetic Peptides—A User's Guide, W.H. Freeman and Company, New York, pp. 259–345.
Kahn Catalytic Asymmetric Cyanohydrin Synthesis, pp. 821–826 (1993).
Kaiser Biochemical Pharmacology 36(6): 783–788 (1987).
Laskowski et al. Ann. Rev. Biochem. 49: 593–626 (1980).
Nakanishi et al. Gene 137: 51–56 (1993).
Ngo et al. The Protein Foling Problem and Tertiary Structure Prediction, pp. 491–495 (1994).
Piela et al. J. Am. Chem. Soc. 4477–4485 (1987).
Ruoslahti et al. Science 238: 491–497 (1987).
Schwartz FEBS Letters 200(1): 1–10 (1986).

(List continued on next page.)

Primary Examiner—Michael Borin
(74) Attorney, Agent, or Firm—Foley & Lardner

(57) ABSTRACT

Among other things, methods of obtaining putative protein-protein interaction sites of biologically-active polypeptides are provided. The methods include searching the polypeptides for a regions that are flanked on each termini by at least one proline residue; and isolating or producing the flanked regions.

9 Claims, No Drawings

OTHER PUBLICATIONS

Thornton et al. Current Opinion in Biotechnology 6(4): 367–369 (1995).
Van Seuningen et al. J. Biol. Chem. 270(45) 26976–26985 (1995).
Wood et al. Int. J. Peptide Protein Res. 39: 533–539 (1992).
Wu et al. J. Biol. Chem. 264(29): 17469–17475 (1989).
Wu et al. Protein Engineering 6(5): 471–478 (1993).
Altieri et al. Journal of Biological Chemistry 268(3): 1847–1853 (1995).
Arai et al. Annu. Rev. Biochem. 59: 783–836 (1990).
Bullesbach et al. Journal of Biological Chemistry 267(32): 22957–22960 (1992).
Cierniewski et al. Biochemistry 31(17): 4248–4253 (1992).
Clark–Lewis et al. Journal of Biological Chemistry 266(34): 23128–23134 (1991).
De Weille et al. Proc. Natl. Acad. Sci. 88: 2437–2440 (1991).
Frank et al. Hoppe–Seyler's Z. Physiol. Chem., BD. 357, S. 590–592 (1976).
Fublendorff et al. Journal of Biological Chemistry 265: 11706–11712 (1990).
Iwasaki et al. FEBS 331(1.2): 187–192 (1993).
Jenny et al. Proc. Natl. Acad. Sci. USA 84: 4846–4850 (1987).
Iyengar et al. Eur. J. Biochem. 96: 193–204 (1979).
Kakar et al. Cloning, Sequencing, and Expression of Human Gonadotropin Releasing Hormone Receptor, pp. 289–295 (1992).
Keck et al. Science 246: 1309–1310 (1989).
Keller et al. Journal of Biological Chemistry 267(30): 6899–6904 (1992).
Keller et al. Journal of Biological Chemistry 268 (8): 5450–5456 (1993).
Kini et al. Current Topics in Peptide & Prot. Res. 1: 297–311 (1994).
Kitakuni et al. Proc. 12th American Peptide Symposium, Cambridge, pp. 378–380 (1991).
Kitamura et al. Biochemical and Biophysical Research Communications 192(2): 553–560 (1993).
Kuo et al. Journal of Biological Chemistry 265(31): 18749–18752 (1990).
Lackman et al. Journal of Immunology 150(7): 2981–2991 (1993).
Larosa et al. Journal of Biological Chemistry 267(35): 25402–25406 (1992).
Layton et al. Journal of Biological Chemistry 266(35): 23815–23823 (1991).
Lerner et al. Journal of Biological Chemistry 267(2): 1062–1066 (1992).
Lin et al. Science 260: 1130–1131 (1993).
Liu et al. J. Biochem. 211: 281–287 (1993).
Mukherjee et al. Design of Immmunomodulatory Peptides Based on Active Site Structures, Chemical and Structural Approaches to Rational Drug Design 237–61 (1995).
Murasugi et al. Journal of Biological Chemistry 266(4): 2486–2493 (1991).
Nosh et al. Protein Stability and Stabilization Through Protein Engineering, Ellis Horwood, N.Y., p. 157 (1991).
Plow et al. Proc. Natl. Acad. Sci. USA 82: 8057–8061 (1985).
Remold–O'Donnell et al. Proc. Natl. Acad. Sci. USA 89: 5635–5639 (1992).
Rose et al. Proc. Natl. Acad. Sci. USA 88: 8641–8645 (1991).
Ryan et al. J. Biol. Chem. 264: 20283–20287 (1989).
Scarborough et al. Journal of Biological Chemistry 268(2): 1058–1065 (1993).
Theerasilp et al. Journal of Biological Chemistry 254(12): 6655–6659 (1989).
Thornton et al. Current Opinion in Biotechnology 6: 367–369 (1995).
Timmermans et al. Pharmacological Reviews 45(2) 205–219 (1993).
Tsuji et al. The EMBO Journal 11(13): 4843–4850 (1992).
Usami et al. Proc. Natl. Acad. Sci. USA 90: 928–932 (1993).
Van Seuningen et al. J. Biol Chemistry 270: 26976–26985.
Walter et al. Journal of Biological Chemistry 267(28): 20371–20376 (1992).
Weiser et al. Proc. Natl. Acad. Sci. USA 86: 7522–7526 (1989).
Wood et al. Int. J. Peptide Protein Res. 39: 533–539 (1992).
Wu et al. J. Biol. Chem. 264: 17469–17475.
Wu et al. Protein Engineering 6(5): 471–478 (1993).
Yamachita et al. Journal of Biological Chemistry 265(26): 15770–15775 (1990).
Sioussat et al. Archives of Biochemistry and Biophysics 301(1): 15–20 (1993).
Sueiras–Diaz et al. Tetrahedron Letters 33(19): 2721–2724 (1992).
Yanaihara et al. J. Amer. Chem. Soc. 94: 8243–8244 (1972).

* cited by examiner

POLYPEPTIDES THAT INCLUDE CONFORMATION-CONSTRAINING GROUPS WHICH FLANK A PROTEIN-PROTEIN INTERACTION SITE

This application is a divisional of Ser. No. 08/934,224 filed Sep. 19, 1997, which is a divisional of Ser. No. 08/532,818 filed May 3, 1996, U.S. Pat. No. 5,965,698, which is a 371 PCT/US94/04294 filed Apr. 21, 1994, which is a continuation-in-part of Ser. No. 08/051,741 filed Apr. 23, 1993 ABN, and Ser. No. 08/143,364 filed Oct. 29, 1993 ABN.

BACKGROUND OF THE INVENTION

The present invention relates to improving the bioactivity of a diverse range of peptides and proteins in their various forms (collectively "polypeptides") by employing conformation-constraining residues to flank sites of the polypeptide that are involved in protein-protein interactions.

Protein-protein interactions are crucial to almost every physiological and pharmacological process. These interactions often are characterized by very high affinity, with dissociation constants in the low nanomolar to subpicomolar range. Such strong affinity between proteins is possible when a high level of specificity allows subtle discrimination among closely related structures. The interaction sites of several protein pairs have been identified by strategies such as chemical modification of specific amino acid residues, site-directed mutagenesis, peptide synthesis, X-ray diffraction studies and theoretical approaches.

Certain general structural features have emerged from these studies. For example, some interactions involve more than one interaction site. The phrase "interaction site" is used in this description to denote a site comprised of amino acid residues which is involved in the interaction between two proteins. The high affinities at these interaction sites are attributed to several factors, including shape complementarity, electrostatic and hydrogen bond links, and burial of hydrophobic groups. A protein-protein interaction may involve one or more of these factors at each interaction site.

The amino acids of an interaction site usually constitute a small proportion of the total amino acids present in the polypeptide. Typically, the number of amino acid residues in a single interaction site ranges from three to six. These residues often are connected by the peptide bonds of adjacent residues in a continuous interaction site. Alternatively, the amino acid residues involved in the interaction are not linked directly by peptide bonds, but rather are brought together by the three-dimensional folding of the protein and are known as "discontinuous" sites. Due to this extensive variability, it has been difficult to identify the amino acids of interaction sites.

The chemical nature of the side chains of the amino acid residues contributes significantly to the interaction, although main chain atoms also can be involved. Positively charged residues (such as lysine, arginine and histidine) can associate through salt bridge links with negatively charged residues (such as aspartic acid and glutamic acid). Additionally, the side chains of leucine, isoleucine, methionine, valine, phenylalanine, tyrosine, tryptophan and proline are often involved in hydrophobic interactions. Precise alignment of atoms between the interaction sites of one protein and its partner also allow multiple Van der Waals interactions and thus increase the likelihood of strong binding between the two interaction partners.

Bernstein et al., *Nature* 340: 482 (1989), proposed a role for methionine in protein-protein interactions, whereby clusters of methionine residues in the 54,000 MW signal recognition particle play a key role in the recognition of signal peptides. Because of the unique flexibility of their side chains, methionine residues located on one face of the surface of the amphiphilic helix provide a malleable, nonpolar surface. It was postulated that in the binding process, this surface can adapt itself to peptide partners of various dimensions and thus conform to the structure of the signal peptide. A similar mechanism was suggested for the ability of calmodulin to interact with various protein partners. The binding site of calmodulin contains eight exposed methionine residues. Such flexibility of the side chain of methionine might be attributable to the presence of the sulfur atom.

A large number of proteins are synthesized as inactive precursors and activated in vivo only where and when they are needed. Accordingly, their activity is strictly regulated so as to contribute to the overall control of physiological processes. Some of these proteins are activated by the action of specific proteinases, and the interaction between the cleavage site and the proteinases should be deemed highly specific. Therefore, the regions around these activation sites form another group of protein-protein interaction sites.

As described above, the diverse properties of the various amino acids affect the characteristics of the interaction site, as well as the polypeptide as a whole. One amino acid residue that has wholly unique structural characteristics is proline.

Proline is the only common imino acid found in proteins. The side chain of proline is bonded to the tertiary nitrogen in a cyclic pyrrolidine ring. This ring inhibits free rotation about the $C_\alpha$—N bond and thus restricts the range of allowable conformations of the polypeptide backbone. The pyrrolidine ring also constrains the conformation of the adjacent residues. The imino nitrogen of the proline residue lacks a proton that is required for hydrogen bond formation in both the $\alpha$-helical and $\beta$-pleated sheet conformations. Accordingly, proline is often called a "helix breaker." Additionally, the carbonyl oxygen atom of the amino acid residue immediately preceding proline in the polypeptide is more electronegative than carbonyl oxygen atoms preceding other amino acid residues. As a result, this carbonyl group has an enhanced tendency to accept and form strong hydrogen bonds.

Proline also differs from other amino acid residues in terms of permissible bond configuration. The partial double bond character of peptide bonds prevents free rotation and can result in either cis or trans configurations around the peptide bond. In the cis configuration, the $C_\alpha$ atoms of adjacent amino acid residues are closer than in the trans configuration. This "closeness" often causes steric hindrance between the side chains on the two $C_\alpha$ atoms. Accordingly, almost all peptide bonds are in the trans configuration, so that the $C_\alpha$ atoms of adjacent amino acid residues are separated by the greatest distance possible. In contrast to most amino acids, proline residues can more readily assume cis configurations because the amide nitrogen is part of a ring. Of course, the ring still imposes conformational constraints by inhibiting free rotation around the $\alpha$ carbons of adjoining residues.

Previous studies have implicated proline residues at some interaction sites of certain classes of molecules. Proline has been thought to be required in the interaction site geometry of a class of proteins known as the serine proteinase inhibitors. This proposal was later retracted because proline was not universally present near interaction sites. See Laskowski and Kato, *Ann. Rev. Biochem.* 49: 593–626 (1980). A proline-directed arginyl cleavage at monobasic processing sites has also been proposed. See Schwartz, *FEBS Letts.* 200: 1–10 (1986). About a third of the monobasic processing sites contain a proline residue either just before or just after the basic residue. A proline residue was also found to be important in the processing of the signal peptide of human lysozyme. Several proline-directed kinases which phosphorylate their substrates at the residues that are immediately followed by proline residues have been purified from various sources. In some cases, a proline residue two or three residues before the phosphorylation site also appears to have importance. But these phosphorylation sites include only a few examples. Hence, it was assumed heretofore that proline was involved in only a small number of specific cases.

Proline is known to be a helix breaker because it has a secondary amine group, which cannot form hydrogen bonds with neighboring CO groups as other amino acids do. Still, proline is found in some of the surface helices of soluble proteins. The "kink" induced by the proline may help in helical packing by wrapping the helix around a protein core. Recently, the importance of proline residues in transmembrane helices has been noted. Interestingly, the putative transmembrane helices of ion channel peptides have a proline residue within their sequence. These proline residues tend to be conserved among homologous proteins, while similar transmembrane helices of non-transport proteins seem to be devoid of proline residues. The convex side of a proline-containing helix is packed against neighboring transmembrane helices. The unique geometry of the proline frees a non-hydrogen bonded carbonyl oxygen in the helix backbone for binding to a cation.

Because an interaction site of a polypeptide is so difficult to identify, the interaction sites of most proteins have remained unknown. In one of its aspects, the present invention takes advantage of proline positioning to identify interaction sites of proteins. The unique properties of proline have a stabilizing function which, according to another aspect of the present invention, can be used to engineer novel polypeptides based on biologically-active polypeptides. These biologically-active polypeptides possess a functional activity and include naturally-occurring polypeptides or polypeptides derived therefrom. These novel polypeptides can have improved activities, stabilities or other properties of interest.

SUMMARY OF THE INVENTION

It thus is an object of the present invention to provide polypeptides which can mimic or antagonize an activity of biologically-active polypeptide, such as a naturally-occurring polypeptide or a polypeptide derived therefrom.

It is another object to provide polypeptides having conformation-constraining residues which flank one or more interaction sites of the polypeptide.

It is still another object of the present invention to provide polypeptide regions that act as protein-protein interaction sites.

It is also an object of the invention to provide an approach for identifying and synthesizing peptides containing interaction sites.

It is yet another object of the present invention to provide a method for synthesizing polypeptides that are flanked by conformation-constraining moieties.

In accomplishing these and other objects, there have been provided, in accordance with one aspect of the present invention, analogs of biologically-active polypeptides, such as naturally-occurring polypeptides or polypeptides derived therefrom, comprising an interaction site and conformation-constraining moieties flanking the interaction site. The analog typically is shorter than the biologically-active polypeptide, but this need not always be the case. Preferably, the analogs are no more than 30 amino acid residues long, and the conformation-constraining moieties are within 7 amino acid residues of the interaction site. It is also preferred that the conformation-constraining moieties are proline residues.

The analogs can mimic or antagonize an activity of a biologically-active polypeptide. Analogs are provided for that mimic the activity of hypotensive peptides, fibrinolytic peptides, chemotactic peptides, growth promoter peptides, lymphocyte mitogens, immunomodulator peptides, clot-inducing peptides, cardiac stimulant peptides, sweet peptides, taste-modifier peptides, macrophage activating peptides, anti-tumor peptides, Relaxin, platelet aggregation inhibitors, Leech Antiplatelet Protein, Moubatin, and Alzeimer's disease peptides. Analogs are also provided for that antagonize or inhibit the activity of fertility peptides, inflammatory peptides, platelet derived growth factor, blood proteins, and angiotensin II. The inhibited blood proteins include Factor V, Factor VIIa, Factor VIII, Factor IXa, Factor Xa, fibrinogen, prothrombin, von Willebrand Factor and Platelet Glycoprotein IIb.

Analogs are obtainable, pursuant to the present invention, by the steps of identifying an interaction site of a biologically-active polypeptide, such as a naturally-occurring polypeptide or polypeptide derived therefrom, and obtaining a polypeptide that (i) has a different length than the biologically-active polypeptide and (ii) contains the interaction site of the biologically-active polypeptide flanked by conformation-constraining moieties.

In accordance with another aspect of the present invention, there are provided homologs of biologically-active polypeptides, such as naturally-occurring polypeptides or polypeptides derived therefrom, which have at least one interaction site. The homologs comprise most or all of the sequence of the biologically-active polypeptide along with conformation-constraining moieties flanking the interaction site. The conformation-constraining moieties can be placed in biologically-active polypeptides that lack such moieties altogether or possess such moieties in an undesired location or an undesired form. Preferably, the conformation-constraining moieties comprise proline residues. For example, proline could be used to replace a cysteine that is involved in a disulfide bound when the interaction site is near the cysteine.

The homologs of the present invention can mimic activities of biologically-active polypeptides. In particular, homologs are provided for that mimic the activity of analgesics, appetite suppressants, B-cell differentiating peptides, hypocalcemic agents, hypoglycemic potentiators, hypotensive agents, immune potentiators and somatostatin-like peptides. Additionally, homologs can antagonize or inhibit activities of biologically-active polypeptides. One such homolog is a gastrin-releasing peptide antagonist.

Homologs within the present invention are obtainable by the steps of (i) identifying an interaction site of a biologically-active polypeptide, such as a naturally-occurring polypeptide or polypeptide derived therefrom and (ii) flanking the interaction site with conformation-constraining moieties.

DETAILED DESCRIPTION OF PREFERRED EMBODIMENTS

It now has been discovered that the biological activity of polypeptides can be enhanced several fold by incorporating proline or other conformation-constraining moieties into regions that flank the interaction site(s) of a given polypeptide. Such enhancement in activity makes it possible to design drugs with greater specificity at decreased cost. Proline residues and other conformation-constraining moieties restrict the number of conformations of the polypeptides to increase the likelihood of the favorable conformation occurring.

The term "polypeptide" is used here to denote all pharmacologically-acceptable forms, such as non-toxic acid or base addition salts.

According to the present invention, an "analog" is a polypeptide containing an interaction site that was obtained or derived from a biologically-active polypeptide, but differs in length from the biologically-active polypeptide upon which it is based. An analog that is shorter than the native polypeptide is referred to as a "truncated analog." In accordance with the present invention, the interaction site(s) of an analog are flanked by conformation-constraining moieties. Typically, these analogs are no more than 30 amino acid residues long, preferably, no longer than 25 amino acid residues and, even more preferably, are no longer than 15 amino acid residues. The conformation-constraining moieties should be within 7 amino acid residues of the interaction site. Preferably, the conformation-constraining moieties are within 4 amino acid residues of the interaction site and, even more preferably, within one amino acid residue of the interaction site. Additionally, the amino acids of the interaction site can be changed, preferably in accordance with the conservative substitutions disclosed herein.

The present invention also is useful for constructing "homologs" of biologically-active polypeptides. A homolog has most or all of the sequence of another, biologically-active polypeptide which contains an interaction site, but the interaction site of the homolog is flanked by conformation-constraining moieties in a manner distinct from the other polypeptide. A homolog thus is a variant formed by placing conformation-constraining moieties adjacent or proximate to the interaction site of the homolog, according to the present invention. This can be done even with polypeptides wherein interaction sites are not flanked with such moieties in the native state. Accordingly, conformation-constraining moieties can be employed advantageously with all polypeptides having interaction sites, regardless of whether the polypeptide is of natural, recombinant or synthetic origin. The conformation-constraining moieties employed should be sufficiently adjacent or proximate to the interaction site to permit the moieties to exert influence on the site. Homologs can have lengths that differ from that of the native polypeptide. That is, the homolog can be longer or shorter than the native polypeptide. For example, the homolog can contain amino acids in addition to those present in the native polypeptide. Finally, the amino acids of the interaction site can be changed, preferably in accordance with the conservative substitutions disclosed herein.

As is apparent from the above discussion, the concepts implicated by the terms "analog," "truncated analog" and "homolog" are not mutually exclusive. For example, a homolog according to the present invention could comprise a polypeptide where prolines are inserted in the polypeptide sequence. As stated above, a polypeptide modified in this way can also have amino acids removed from the sequence. Thus, a homolog can be shortened so that its length is less than that of the native polypeptide. Other modifications will become apparent to the skilled artisan in view of the present specification.

The present invention employs to advantage the unique structures and characteristics of proline. In proteins, proline residues often affect the conformation of protein-protein interaction sites by breaking the continuity of the adjacent secondary structures, such as α-helices. Small polypeptides often do not have secondary structures, however. Nevertheless, the presence of proline residues in both large and small peptides is useful, pursuant to the present invention, both for locating the interaction sites of these polypeptide and for stabilizing interaction regions.

The present invention thus encompasses a method for altering or stabilizing the reactivity of interaction sites for bioactivity, by synthesizing a sequence of amino acids where (i) a part of the sequence comprises an interaction site, (ii) the interaction site is flanked on both sides by sequences that contain a proline residue or other conformation-constraining moiety, and (iii) each such moiety is located sufficiently near an interaction site to exert influence over the site. In accordance with the present invention, sequences as thus described can be placed adjacent or proximate to an interaction site on a polypeptide to alter or stabilize the specific reactivity of the site. Such a site can be referred to as being "flanked" or "bracketed" by the conformation-constraining moiety. In this specification, a conformation-constraining moiety so inserted is often referred to as a "bracket."

The present invention also relates to the identification of interaction sites in polypeptides. The interaction site of a polypeptide can be ascertained by searching for flanking proline residues or other conformation-constraining moieties, such as cysteine. For instance, a peptide region that is flanked by two proline residues, a proline residue and a cysteine residue or two cysteine residues is at least a putative interaction site. Typically, the regions that are flanked by these residues comprise fifteen or fewer amino acids.

Via methodology within the present invention, it is possible to produce novel, multifunctional polypeptides, or polypeptides with new functional properties, by inclusion of interaction sites with proline or other conformation-constraining brackets into the polypeptide. The polypeptides of the present invention can be administered in various non-toxic forms, such as acid or base addition salts.

The inclusion of proline or other constraining brackets allows the interaction site to be altered, which permits targeting of the polypeptide to certain interaction partners found on specific cell or tissue types. Targeting of polypeptide drugs to a specific type of cell or tissue would result in considerable reduction of both the effective dose and the likelihood of side effects. Polypeptides can be custom designed, in accordance with the present invention, to flank an interaction site with brackets to alter or otherwise affect the flanked site.

It is often desirable to insert alanine residues adjacent to the proline brackets. That is, the alanine residues would flank the proline-bracketed interaction sites. The alanine residues serve to protect the amino- and carboxy-terminal ends of the polypeptide.

Several polypeptides having specific, desired activity have been identified. Polypeptides of the structures described here can be synthesized routinely, using solid-phase or solution-phase peptide synthesis. The final peptide preparation can be purified using various chromatographic methods including high performance liquid chromatography and adsorption chromatography. The purity and the quality of the peptides can be confirmed by amino acid analyses, molecular weight determination, sequence determination and mass spectrometry.

The analogs and homologs of the present invention can be combined with a variety of carriers. Pharmaceuticallyacceptable carriers include aqueous solutions, non-toxic excipients, including salts, preservatives, buffers and the like, as described in REMINGTON'S PHARMACEUTICAL SCIENCES, 15th Ed. Easton: Mack Publishing Co. pp 1405–1412 and 1461–1487 (1975) and THE NATIONAL FORMULARY XIV., 14th Ed. Washington: American Pharmaceutical Association (1975), the contents of which are hereby incorporated by reference. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the binding composition are adjusted according to routine skills in the art. See GOODMAN AND GILMAN'S THE PHARMACOLOGICAL BASIS FOR THERAPEUTICS (7th ed.).

Structural Modifications

Protein interaction sites in great diversity have been identified via the present invention and are described in greater detail below. These interaction sites and surrounding sequences can be altered further in view of the substitution considerations described below.

Conservative substitutions-Amino acids having similar properties can be employed to make conservative substitutions in the sequence of a polypeptide. Such substitutions can help in retaining or, in some cases, enhancing biological properties of the polypeptides. The replacement of one amino acid residue by another residue of the same group are considered conservative substitutions, as set forth below:

group (a)—Lys, Arg, Homoarg and Orn;
group (b)—Leu, Ile, Val, Met and Norleu;
group (c)—Tyr, Phe and Trp;
group (d)—Glu and Asp;
group (e)—Gln and Asn;
group (f)—Ser and Thr; and
group (g)—Ala and Gly.

The abbreviations are as follows: Ala=alanine; Arg=arginine; Asn=asparagine; Asp=aspartic acid; Gln=glutamine; Glu=glutamic acid; Gly=glycine; His=histidine; Homoarg=homoarginine; Ile=isoleucine; Leu=leucine; Lys=lysine; Met=methionine; Norleu=norleucine; Orn=ornithine; Phe=phenylalanine; Pro=proline; Ser=serine; Thr=threonine; Trp=tryptophan; Tyr=tyrosine and Val=valine.

It must be noted, however, that the greater the number of substitutions made in the interaction site, the less predictable its activity will be. Generally, it is preferred to make no more than two amino acid substitutions in the sequence of a given interaction site. In some biologically-active polypeptides, both is proline residues and disulfide bridges serve to constrain the conformation of interaction sites. A naturally-occurring interaction site may be bracketed by (1) two proline residues, (2) a proline residue and a cysteine residue (in a disulfide linkage) or (3) two cysteine residues in disulfide linkage, either in linkage with each other or with other residues in the polypeptide, as appropriate.

In most of the polypeptides structures presented here, the proline residues are employed as non-cyclic structural constraints. This means that the constraining proline brackets are only bound to other amino acids by the peptide bond. The present invention also comprehends other non-cyclic structural constraints, such as L-N-methylated amino acid residues or spirolactams. These moieties can be introduced into the peptide backbone. Additionally, side chains can be cyclized to the backbone so as create a L-γ-lactam moiety an each side of the interaction site. See, generally, Hruby et al., "Applications of Synthetic Peptides," in SYNTHETIC PEPTIDES: A USER'S GUIDE 259–345 (W. H. Freeman & Co. 1992). Cyclization also can be achieved, for example, by formation of cystine bridges, coupling of amino and carboxy terminal groups of respective terminal amino acids, or coupling of the amino group of a Lys residue or a related homolog with a carboxy group of Asp, Glu or a related homolog. Coupling of the α-amino group of a polypeptide with the ε-amino group of a lysine residue, using iodoacetic anhydride, can be also undertaken. See Wood and Wetzel, *Int'l J. Peptide Protein Res.* 39: 533–39 (1992).

The conformational restraints imposed by cyclization arise from covalent cross-linking may reduce flexibility too much and even result in strain at the interaction site, which could lead to a loss of function. Proline brackets, on the other hand, allow for some flexibility without causing significant strain at the interaction site. Accordingly, proline is preferred for use in the present invention.

A key aspect of the present invention is the recognition that smaller polypeptides show a considerable amount of flexibility and, consequently, can exist in solution in a very high number of conformers, generated by rotation around all of the N—$C_\alpha$ and $C_\alpha$—C bonds of the peptide backbone. Pursuant to the present invention, the bracketing of an interaction site by either L- or D-proline imposes constraints on the polypeptide, thereby reducing the number of possible conformers and increasing the relative population that has the favored, active conformation. The introduction of proline brackets to alter or stabilize bioactivity at interaction sites can potentiate the specific action of drugs and other biologically-active agents.

Synthesis of Peptides

Polypeptides within the present invention can be generated directly from the native polypeptides by chemical cleavage, by proteolytic enzyme digestion, and by combinations thereof. Additionally, such polypeptides can be created by synthetic techniques or recombinant techniques which employ genomic or cDNA cloning methods.

For example, methods of synthesizing polypeptides directly from amino acid derivatives are widely known. Such synthesis can be undertaken with automated peptide synthesizers. Peptides of the structures given below can be routinely synthesized using solid phase or solution phase peptide synthesis.

Site-specific and region-directed mutagenesis techniques also can be employed. See CURRENT PROTOCOLS IN MOLECULAR BIOLOGY vol. 1, ch. 8 (Ausubel et al. eds., J. Wiley & Sons 1989 & Supp. 1990–93); PROTEIN ENGINEERING (Oxender & Fox eds., A. Liss, Inc. 1987). In addition, linker-scanning and polymerase chain reaction ("PCR") mediated techniques can be used for purposes of mutagenesis. See PCR TECHNOLOGY (Erlich ed., Stockton Press 1989); CURRENT PROTOCOLS IN MOLECULAR BIOLOGY, vols. 1 & 2, loc. cit.

The final peptide preparation can be purified using various chromatographic methods including high performance liquid chromatography and adsorption chromatography. The purity and the quality of the peptides can be confirmed by amino acid analyses, mass spectrometry, molecular weight determination and sequence determination.

Polypeptides within the present invention can be administered in the manner that natural peptides are administered.

The method of administration will depend on the site at which the reaction is to occur, as well as the desired result.

The present invention is further illustrated by the following examples. These examples concern the interaction sites of various types of proteins, and are provided to give further insights into the invention. These examples do not limit the scope of the invention.

EXAMPLE I

Effects of Proline on Cellular Adhesion Proteins

Cellular adhesive interactions are involved in tissue development, hemostasis, tumor cell metastasis, intercellular communication, and host defense mechanisms of multicellular organisms. The recognition of extracellular ligands by cell surface receptors is a common but mandatory step in such interactions.

Most of these interactions are mediated by a family of closely related adhesive receptors and have therapeutic implications. For example, the development of antiplatelet drugs is important in the prevention and treatment of atherosclerosis, myocardial infarction, stroke and cancer. The polypeptides involved in platelet aggregation and other adhesive interactions are structurally and immunologically related, and platelet aggregation, one of the specialized adhesive reactions, is easy to monitor by conventional techniques.

Several recognition sequences are involved in the adhesive interactions. The Arg-Gly-Asp (RGD) (SEQ ID NO: 1) tripeptide is a common molecular recognition site implicated in several of these interactions. But the presence of the RGD sequence alone does not necessarily result in the participation of the proteins in adhesive reactions. It appears that the presence of other amino acid residues around the RGD sequence may be important for the presentation of this site. Most adhesive proteins contain at least one proline residue around the RGD sequence, one notable exception being fibrinogen.

Other classes of proteins, such as the disintegrins, possess the RGD tripeptide. Disintegrins are a family of very potent platelet aggregation inhibitors isolated from venoms. These proteins interfere in the interaction between fibrinogen and the glycoprotein IIb–IIIa complex. The RGD sequence in disintegrins is located at the tip of a loop and is accessible for interaction. Several disintegrins and related inhibitors also contain proline residues.

The effectiveness of proline brackets was demonstrated by constructing several small RGD peptides. Small peptides containing the RGD sequence inhibit adhesive reactions, including platelet aggregation. The sequence Ile-Ala-Arg-Gly-Asp-Met-Asn-Ala was selected as typical of peptides containing the Arg-Gly-Asp sequence. Proline residues were substituted on one or both sides of the Arg-Gly-Asp-Met sequence. Four peptides, Ile-Ala-Arg-Gly-Asp-Met-Asn-Ala (P-1) (SEQ ID NO: 2), Ile-Pro-Arg-Gly-Asp-Met-Asn-Ala (P-2) (SEQ ID NO: 3), Ile-Ala-Arg-Gly-Asp-Met-Pro-Ala (P-3) (SEQ ID NO: 4), and Ile-Pro-Arg-Gly-Asp-Met-Pro-Ala (P-4) (SEQ ID NO: 5), were synthesized by solid phase peptide synthesis. After extraction, the peptides were purified by a reverse phase HPLC system to more than 95% purity, with yields between 80% and 90%. The structures of individual peptides were confirmed by amino acid analysis, and their masses were confirmed by fast atom bombardment mass spectra.

The inhibition of platelet aggregation by these peptides was studied in a whole blood aggregometer. Platelet aggregations were initiated by the addition either of collagen or of ADP. All four peptides inhibited platelet aggregation.

To compare the inhibitory potencies, the dose-response relationships were determined for the polypeptides, as identified below in Table 1. The inhibitory potencies of the polypeptides were P-4>P-3=P-2>P-1. The concentration of polypeptides inhibiting platelet aggregation by 50% ("the $IC_{50}$ value") was determined from the dose-response curves; the fold-increase in the inhibitory potencies also was determined (Table 1). The inhibitory potency of Ile-Ala-Arg-Gly-Asp-Met-Asn-Ala is comparable with that of the Arg-Gly-Asp-Ser peptide (SEQ ID NO: 6). Incorporation of proline on either side of Arg-Gly-Asp enhances the potency to about the same extent. Inclusion of proline residues on both sides enhanced the antiplatelet effect of the Arg-Gly-Asp peptide by 7 to 13-fold.

TABLE 1

| Peptide | Donor 1 | | Donor 2 | |
|---|---|---|---|---|
| | IC50 | Fold | IC50 | Fold |
| Collagen-induced aggregation | | | | |
| P-1 | 84.5 | — | 67.3 | — |
| P-2 | 48.8 | 1.73 | 27.6 | 2.44 |
| P-3 | 37.5 | 2.25 | 27.6 | 2.44 |
| P-4 | 6.4 | 13.10 | 8.4 | 8.01 |
| Arg—Gly—Asp—Ser | 57.8 | — | 32.3 | — |
| ADP-induced aggregation | | | | |
| P-1 | 27.3 | — | 22.5 | — |
| P-2 | 21.5 | 1.27 | 18.9 | 1.19 |
| P-3 | 21.0 | 1.30 | 16.7 | 1.34 |
| P-4 | 4.0 | 6.77 | 2.2 | 10.27 |
| Arg—Gly—Asp—Ser | 29.9 | — | 13.8 | — |

The inhibitory potency of P-2, P-3, and P-4 were compared with P-1 to obtain the fold increase in its potency.

There are other RGD-containing peptides that inhibit the interaction between fibrinogen and its platelet receptor, the glycoprotein IIb–IIIa complex, and thus are platelet aggregation inhibitors. These peptides can be administered by intravenous injections, in situ injections, local applications, inhalation, oral administration using coated polymers, dermal patches or other appropriate means, usually in a dosage of 100–2000 nM. Sequences include:

Ile-Pro-Arg-Gly-Asp-Tyr-Pro-Ala (PYP) (SEQ ID NO: 7)

Ile-Pro-Arg-Gly-Asp-Phe-Pro-Ala (PFP) (SEQ ID NO: 8)

Ile-Pro-Arg-Gly-Asp-Trp-Pro-Ala (PWP) (SEQ ID NO: 9)

Ile-Pro-Lys-Gly-Asp-Trp-Pro-Ala (PKWP) (SEQ ID NO: 10)

Ile-Pro-Homoarg-Gly-Asp-Trp-Pro-Ala (PhRWP) (SEQ ID NO: 11)

Each of these peptides have the generalized formula (SEQ ID NOS: 146 and 147, respectively) b-Pro-a-g-d-b or c-Pro-g based on the conservative substitution groups discussed above.

Another important interaction site on adhesive proteins is the sequence Leu-Asp-Val (SEQ ID NO: 12 wherein proline brackets are provided to form the sequence Ala-Pro-Leu-Asp-Val-Pro-Ala (SEQ ID NO: 13). Additionally, the interaction site having the sequence Val-Thr-Cys-Gly (SEQ ID NO: 14) can be bracketed providing the sequence Ala-Pro-Val-Thr-Cys-Gly-Pro-Ala (SEQ ID NO: 15).

These data demonstrate that the inclusion of conformation-constraining moieties can have desirable effects on an interaction site. These data also demonstrate that interaction sites possess activity when present in a polypeptide that differs from the native form. Finally, these data show the propriety of identifying interaction sites by the presence of proline brackets. Accordingly, the below-described analogs and homologs of the present invention, which contain conformation-constraining brackets like proline, have useful activities.

EXAMPLE II

Truncated Analogs

The following sequences are obtained from naturally-occurring polypeptides that contain proline brackets or proline/cysteine brackets. These polypeptides can be shortened to form fragments that contain one or more interaction sites of interest. As stated above, these fragments are referred to as "truncated analogs."

The presence of the proline brackets is useful for identifying the interaction sites of the polypeptides to permit construction of the truncated analogs. The truncated analogs below can be employed in a manner similar to the naturally-occurring polypeptide. In this sense, the truncated analogs mimic the naturally-occurring polypeptide.

Hypotensive Peptides

Applications: Treatment of cardiovascular diseases by reduction of blood pressure.

1. Origin Type: Calciseptine

Mechanism: Binds to L-type calcium channels in aorta and cardiac myocytes and inhibits the calcium current. This helps in the relaxation of these muscles and thus reduces blood pressure.

Dose: 60 to 120 µg per rat (5 to 10 µM). Comparable to diltiazem (in Cardizem-CD), which is on the market.

Advantages: Preliminary studies indicate that in the presence of diltiazem there is a small increase in the diastolic pressure. This suggests incomplete relaxation of the heart between beats when treated with diltiazem, which is detrimental. Treatment with the peptide, however, does not increase diastolic pressure. Also the peptide seems to exert anti-arrythmogenic activity.

Administration: Intravenous injections, inhalation, coated polymers (oral), implants, skin patches, and other appropriate means.

Structure:
Ala-Pro-Thr-Ala-Met-Trp-Pro-Ala (HP-1 or L-Calchin) (SEQ ID NO: 16)

2. Origin Type: Adrenomedulin

Mechanism: Reduces the blood pressure in rats through an unknown mechanism, possibly involving nerve terminals.

Dose: 30 to 100 µg/rat (30 to 100 nmole/rat)

Advantages: Increases cyclic AMP in platelets and may thus possess antiplatelet activity. Such antiplatelet activity is beneficial in reducing the risk of myocardial infarction and stroke in individuals with high blood pressure.

Administration: Intravenous injections, inhalation, coated polymers (oral), implants, skin patches and other appropriate means.

Structure:
Ala-Pro-Arg-Ser-Lys-Ile-Ser-Pro-Gln-Gly (HP-2 or Amulin) (SEQ ID NO: 17)

3. Origin Type: Maxadilan

Mechanism: Reduces blood pressure through vasodilation.

Dose: 200–500 nM (10 µg/rat).

Administration: Intravenous injections, inhalation, coated polymers (oral), implants and skin patches.

Structures:
Gln-Leu-Pro-Gly-Asn-Ser-Val-Phe-Lys-Glu-Pro-Met (HP-3 or Dilamax-1) (SEQ ID NO: 18)
Phe-Thr-Ser-Met-Asp-Thr-Ser-Gln-Leu-Pro-Gly (HP-4 or Dilamax-2) (SEQ ID NO: 19)

Fibrinolytic Peptides

Application: For dissolving clots formed in various thrombotic and hemostatic ailments including myocardial infarction and stroke.

Mechanism: Binds to plasminogen and non-proteolytically activates plasminogen, which dissolves fibrin clot.

Dose: 1–300 µM.

Administration: Intravenous injections, in situ injections, local applications, inhalation, oral administration using coated polymers, dermal patches and other appropriate means.

1. Origin Type: Staphylokinase

Structures:
Ser-Pro-Arg-Tyr-Val-Glu-Phe-Pro-Ile-Lys-Pro-Gly (FP-STA1) (SEQ ID NO: 20)
Phe-Pro-Ile-Thr-Glu-Lys-Gly-Phe-Val-Val-Pro-Asp (FP-STA2) (SEQ ID NO: 21)
Val-Pro-Asp-Leu-Ser-Glu-His-Ile-Lys-Asn-Pro-Gly (FP-STA3) (SEQ ID NO: 22)
Lys-Pro-Asp-Asp-Ala-Ser-Tyr-Phe-Glu-Pro-Thr-Gly-Pro-Tyr (FP-STA4) (SEQ ID NO: 23)

2. Origin Type: Streptokinase

Structures:
Arg-Pro-Tyr-Lys-Glu-Lys-Pro-Val (FP-SRP1) (SEQ ID NO: 24)
Thr-Pro-Leu-Asn-Pro-Asp-Asp-Asp-Phe-Arg-Pro-Gly (FP-SRP2) (SEQ ID NO: 25)
Ser-Pro-Lys-Ser-Lys-Pro-Phe-Ala-Thr-Asp-Ser-Gly-Ala-Met-Pro-His (FP-SRP3) (SEQ ID NO: 26)

Chemotactic Peptides

Applications: Attract neutrophils and macrophages and hence will be useful in enhancing body defense mechanism at a required site.

Mechanism: Probably through specific receptor interaction.

Administration: Intravenous injections, in situ injections, local applications, inhalation, oral administration using coated polymers, dermal patches and other appropriate means.

1. Origin Type: CP-10
Dose: 10–100 pM
Structure:
Ala-Pro-Gln-Phe-Val-Gln-Asn-Ile-Pro-Ala (CP-CP10A) (SEQ ID NO: 27)

2. Origin Type: lnterleukin-β
Dose: 5–100 nM
Structure:
Lys-Glu-Leu-Arg-Pro-Gln (CP-IL8A) (SEQ ID NO: 28)
Origin Type: α-1 Proteinase Inhibitor
Dose: 5–100 nM
Structures:
Ala-Pro-Glu-Val-Lys-Phe-Asn-Lys-Pro-Phe-Val (CP-αPI1) (SEQ ID NO: 29)
Ser-Pro-Leu-Phe-Ile-Gly-Lys-Val-Val-Asn-Pro-Thr (CP-αPI2) (SEQ ID NO: 30)

Growth Promoter Peptides

Neurite-promoting Peptides

Applications: In treatment of injuries to nervous system and trauma. Helpful in promoting growth of neurites to regenerate broken connections caused by injury.

1. Origin Type: Pleiotrophin

Mechanism: Through interaction with specific receptors.

Dose: 50 to 200 nM.

Advantages: Smaller size of the peptide may help the molecule cross the blood-brain barrier.

Administration: Intravenous injections, in situ injections, inhalation, oral administration using coated polymers, dermal patches and other appropriate means.

Structures:

Ser-Lys-Pro-Ala-Gly-Lys-Leu-Thr-Lys-Ser-Lys-Pro-Gln-Ala (NPP-PT1) (SEQ ID NO: 31)

Ser-Lys-Pro-Ala-Gly-Lys-Leu-Thr-Lys-Pro-Lys-Pro-Gln-Ala (NPP-PT2) (SEQ ID NO: 32)

Lys-Ile-Pro-Ala-Asn-Trp-Lys-Lys-Gln-Phe-Pro-Ala (NPP-PT3) (SEQ ID NO: 33)

Homology: The NPP-PT1 and NPP-PT2 polypeptides have the generalized formula (SEQ ID NO:148) f-a-Pro-g-g-a-b-f-a based on the conservative substitution groups discussed above.

2. Origin Type: Ciliary Neurotrophic Factor

Mechanism: Probably through specific receptors.

Dose: 5–200 nM.

Advantages: Smaller size of the peptide may help the molecule cross the blood-brain barrier.

Administration: Intravenous injections, in situ injections, inhalation, oral administration using coated polymers, dermal patches and other suitable means.

Structures:

Val-Pro-Val-Ala-Ser-Thr-Asp-Arg-Trp-Ser-Glu-Leu-Thr-Glu-Ala (NPP-CNTF1) (SEQ ID NO: 34)

Ile-Pro-Arg-Asn-Glu-Ala-Asp-Gly-Met-Pro-Ile (NPP-CNTF2) (SEQ ID NO: 35)

Granulocyte Colony Stimulating Peptides

Applications: Helpful in proliferation and differentiation of hemopoietic precursors and stimulation of mature cells. For treatment of neutropenia in a variety of clinical situations.

Mechanism: Through interaction with specific receptors.

Dose: 50 to 200 nM.

Administration: Intravenous injections, in situ injections, inhalation, oral administration using coated polymers, dermal patches and other appropriate means.

1. Origin Type: GCSP

Structures:

Ala-Pro-Ser-Gln-Ala-Leu-Gln-Leu-Ala-Pro-Ala (GCSP-1) (SEQ ID NO: 36)

Ala-Pro-Ala-Leu-Gln-Pro-Thr-Gln-Gly-Ala-Met-Pro-Ala (GCSP-2) (SEQ ID NO: 37)

Ile-Pro-Trp-Ala-Pro-Leu-Ser-Ser-Ala-Pro-Ser (GCSP-3) (SEQ ID NO: 38)

Ser-Pro-Glu-Leu-Gly-Pro-Thr-Leu (GCSP-4) (SEQ ID NO: 39)

Thr-Pro-Leu-Gly-Pro-Ala-Ser-Ser-Leu-Pro-Gln-Ser (GCSP-5) (SEQ ID NO: 40)

2. Origin Type: IL-3

Structure:

Leu-Pro-Leu-Ala-Thr-Ala-Ala-Pro-Thr-Arg-His-Pro-Ile (IL3A) (SEQ ID NO: 41)

Progen (SCF Peptides)

Applications: Helpful in proliferation and differentiation of hemopoietic precursors and stimulation of mature cells. For treatment after bone marrow transplants and various other clinical situations.

Origin Type: Stem Cell Factor

Mechanism: Interact with specific receptors and enhance the growth and differentiation of progenitor cells.

Dose: 100 to 500 nM.

Administration: Intravenous injections, in situ injections, inhalation, oral administration using coated polymers, dermal patches and other suitable means.

Structures:

Asp-Pro-Val-Val-Ser-Ser-Thr-Leu-Ser-Pro-Glu (SCF-1; Progen-1) (SEQ ID NO: 42)

Val-Pro-Gly-Met-Asp-Val-Leu-Pro-Ser (SCF-2; Progen-2) (SEQ ID NO: 43)

Ser-Pro-Glu-Pro-Arg-Leu-Phe-Thr-Pro-Glu (SCF-3; Progen-3) (SEQ ID NO: 44)

Endothelial Growth Peptides

Applications: For inducing growth of vasculature. Helpful in wound healing after surgical procedures as well as in severe damage caused by accidents.

Origin Type: Vascular Permeability Factor

Dose: 50 to 300 nM.

Administration: Intravenous injections, in situ injections, topical application, inhalation, oral administration using coated polymers, dermal patches or other suitable means.

Structure:

Tyr-Pro-Asp-Glu-Ile-Glu-Tyr-Ile-Phe-Lys-Pro-Ser (VPF-1) (SEQ ID NO: 45)

Neurotrophic Factor

Applications: For treatment of injuries and trauma to the nervous system. Helpful in promoting growth of neurites to regenerate broken connections caused by injury.

Origin Type: Glial Cell Line-Derived Neurotrophic Factor

Mechanism: Promotes the growth of dopaminergic neurons through interaction with specific receptors.

Dose: 50 to 200 nM.

Advantages: The small size of the peptide may help the molecule cross the blood-brain barrier.

Administration: Intravenous injections, in situ injections, inhalation, oral administration using coated polymers, dermal patches and other appropriate means.

Structures:

Ser-Pro-Asp-Lys-Gln-Ala-Ala-Ala-Leu-Pro-Arg-Arg (NPP-GDNF1) (SEQ ID NO: 46)

Asn-Pro-Glu-Asn-Ser-Arg-Pro-Lys (NPP-GDNF2) (SEQ ID NO: 47)

Lymphocyte Mitogens

Origin Type: Streptococcus pyrogenes Mitogenic Factor

Dose: 1 to 100 µM.

Administration: Intravenous injections, in situ injections, inhalation, oral administration using coated polymers, dermal patches and other appropriate means.

Structures:

Thr-Pro-Ala-Leu-Phe-Pro-Lys (LM-SP1) (SEQ ID NO: 48)

Asn-Pro-Ala-Gly-Trp-Thr-Gly-Asn-Pro-Asn (LM-SP2) (SEQ ID NO: 49)

Ala-Pro-Ile-Tyr-Asn-Ala-Asp-Glu-Leu-Ile-Pro-Arg (LM-SP3) (SEQ ID NO: 50)

Immunomodulator Peptides

1. Origin Type: Ling-Zhi-8

Applications: Combating several inflammatory autoimmune diseases and others. Antidiabetic and antitumor effects.

Mechanism: Activate T-cells and facilitate cellular interaction.

Dose: 10–150 nM.

Administration: Intravenous injections, in situ injections, inhalation, oral administration using coated polymers, dermal patches and other appropriate means.

Structures:

Tyr-Thr-Pro-Asn-Trp-Gly-Arg-Gly-Asn-Pro-Asn-Asn (IP-LZ1) (SEQ ID NO: 51)

Gly-Asn-Pro-Asn-Asn-Phe-Ile-Asp-Thr-Val-Thr-Phe-Pro-Lys-Val (IP-LZ2) (SEQ ID NO: 52)

2. Origin Type: IL-4

Mechanism: Bind to specific receptors and inhibit cell-mediated immunity, enhances humoral immunity.

Dose: 10–500 nM.

Administration: Intravenous injections, in situ injections, inhalation, oral administration using coated polymers, dermal patches and other appropriate means.

Structures:

Leu-Pro-Val-Thr-Asp-Ile-Phe-Ala-Ala-Pro-Lys (IP-IL4A) (SEQ ID NO: 53)

Ala-Pro-Val-Lys-Glu-Ala-Asn-Gln-Pro-Thr (IP-IL4B) (SEQ ID NO: 54)

Thr-Pro-Ala-Thr-Glu-Leu-Thr-Val-Pro-Asp (IP-IL4C) (SEQ ID NO: 55)

Ser-Pro-His-Glu-Lys-Asp-Thr-Arg-Pro-Leu (IP-IL4D) (SEQ ID NO: 56)

3. Origin Type: IL-10

Mechanism: Bind to specific receptors and inhibit cell-mediated immunity, enhances humoral immunity.

Dose: 10–500 nM.

Administration: Intravenous injections, in situ injections, inhalation, oral administration using coated polymers, dermal patches and other appropriate means.

Structures:

Val-Pro-Gln-Ala-Glu-Asn-Gln-Asp-Pro-Asp-Ile (IP-IL10A) (SEQ ID NO: 57)

Arg-Pro-His-Arg-Phe-Leu-Pro-Ala (IP-IL10B) (SEQ ID NO: 58)

His-Phe-Pro-Gly-Asn-Leu-Pro-Asn-Met-Leu (IP-IL10C) (SEQ ID NO: 59)

Clot-inducing Peptides

Applications: Effective in controlling blood loss in various situations, including surgical procedures and accidents.

1. Origin Type: Staphylocoagulase

Mechanism: Bind and non-proteolytically activate pro-thrombin which in turn induces blood clotting.

Dose: 1–200 μM.

Administration: Topical applications by spraying at the site of the damage.

Structures:

Thr-Pro-Ala-Ile-Asp-Leu-Leu-Glu-Thr-Tyr-Lys-Tyr-Gly-Asp-Pro-Ile (CIP-STA1) (SEQ ID NO: 60)

Asp-Pro-Ile-Tyr-Lys-Glu-Ala-Lys-Asp-Arg-Leu-Met-Thr-Arg (CIP-STA2) (SEQ ID NO: 61)

Asn-Pro-His-Lys-Ile-Thr-Asn-Glu-Arg-Ile-Lys (CIP-STA3) (SEQ ID NO: 62)

Glu-Leu-Arg-Ala-Lys-Leu-Asp-Leu-Ile-Leu-Pro-Asp (CIP-STA4) (SEQ ID NO: 63)

Ser-Pro-Val-Val-Lys-Glu-Glu-Asn-Lys-Val-Glu-Glu-Pro-Gln-Leu (CIP-STA5) (SEQ ID NO: 64)

2. Origin Type: Botrocetin

Mechanism: Interact with von Willebrand factor and/or glycoprotein Ib and induce platelet aggregation.

Dose: 1–200 μM.

Applications: Effective in controlling blood loss in various situations, including surgical procedures and accidents.

Administration: Topical applications by spraying at the site of the damage.

Structures:

Lys-Pro-Thr-Asn-Asn-Lys-Trp-Trp-Ile-Ile-Pro-Ala (CIP-BCTN1) (SEQ ID NO: 65)

Ala-Pro-Ser-Gly-Trp-Ser-Ser-Tyr-Glu-Gly-Asn-Pro-Tyr (CIP-BCTN2) (SEQ ID NO: 66)

Asn-Pro-Phe-Val-Ala-Lys-Ser-Pro-Ala (CIP-BCTN3) (SEQ ID NO: 67)

Cardiac Stimulant Peptides

Origin Type: Anthopleurin A and B

Mechanism: Bind to voltage-gated sodium channels and prolong the action potential, which causes cardiostimulatory effects.

Dose: 50–1000 nM.

Administration: Intravenous injections, inhalation, oral administration using coated polymers, dermal patches and other appropriate means.

Structures:

Arg-Pro-Arg-Gly-Asn-Thr-Leu-Ser-Pro-Ala (CSP-APB1) (SEQ ID NO: 68)

Gly-Pro-Ser-Val-Arg-Gly-Asn-Thr-Leu-Ser-Pro-Ala (CSP-APA1; Aleurin) (SEQ ID NO: 69)

Homology: The CSP-APA1 and CSP-APB1 polypeptides have the generalized formula (SEQ ID NO: 144) a-g-e-f-b-f-Pro-g based on the conservative substitution groups discussed above.

Sweet Peptides

Applications: As non-nutrient sweeteners for food, drink, desserts, candies, chewing gums and medicine. Helpful in both normal and low calorie diets for reducing calorie intake. Useful in making bitter medicine and pills more palatable. Suitable for persons with diabetes.

Mechanism: These peptides bind to receptors of sweet tasting papillae and induce a sweet sensation.

Dose: Typically, these peptides are 5000 to 10,000 times sweeter than sugar. In comparison, aspartame is only 160 times sweeter than sugar.

Administration: Oral

Modifications: Other structural constraints, particularly cyclization, may improve the heat stability of these peptides. Stabilization should increase the usefulness of these polypeptides in cooking.

1. Origin Type: Thaumatin

Structures:

Ala-Pro-Ala-Lys-Leu-Lys-Ala-Pro-Gly (SW-T1) (SEQ ID NO: 70)

Ala-Pro-Gly-Ser-Ser-Asn-Tyr-Arg-Val-Thr-Phe-Ala-Pro-Thr-Ala (SW-T2) (SEQ ID NO: 71)

Gly-Pro-Thr-Glu-Tyr-Ser-Arg-Phe-Phe-Lys-Arg-Leu-Ala-Pro-Asp (SW-T3) (SEQ ID NO: 72)

Asp-Lys-Pro-Thr-Thr-Val-Thr-Ala-Pro-Gly (SW-T4) (SEQ ID NO: 73)

Asn-Val-Pro-Met-Asn-Phe-Ser-Pro-Thr-Thr (SW-T5) (SEQ ID NO: 74)

2. Origin Type: Monellin

Structures:

Ile-Arg-Pro-Ala-Met-Lys-Lys-Thr-Ile-Tyr-Glu-Asn-Glu (SW-M1) (SEQ ID NO: 75)

Arg-Pro-Arg-Lys-Leu-Leu-Arg-Phe-Asn-Gly-Pro-Val (SW-M2) (SEQ ID NO: 76)

3. Origin Type: Mabinlin
Structures:
Gln-Pro-Arg-Arg-Pro-Ala-Leu-Arg-Gln-Pro-Ala (SW-MB1) (SEQ ID NO: 77)
Ala-Pro-Asn-Gln-Leu-Arg-Gln-Val-Asp-Arg-Pro-Ala (SW-MB2) (SEQ ID NO: 78)
Ile-Pro-Asn-Ile-Gly-Ala-Ala-Pro-Phe-Arg-Ala-Trp (SW-MB3) (SEQ ID NO: 79)
Ile-His-Arg-Arg-Ala-Gln-Phe-Gly-Gly-Gln-Pro-Asp (SW-MB4) (SEQ ID NO: 80)
Leu-Pro-Asn-Ile-Ala-Asn-Ile-Pro-Asn (SW-MB5) (SEQ ID NO: 81)

Taste-Modifier Peptides

Applications: As modifiers of sour taste into sweet taste.
Mechanism: Probably through interaction with taste receptors.
Dose: 30 nM to 500 nM.
Administration: Oral.
Modifications: Structural constraints, particularly cyclization of the peptides, may help in the heat stability of these peptides. Stabilization should increase the usefulness of these polypeptides in cooking.

1. Origin Type: Miraculin
Structures:
Asp-Arg-Pro-Leu-Ala-Phe-Phe-Pro-Glu-Asn-Pro-Lys-Glu (TM-MIR1) (SEQ ID NO: 82)
Thr-Thr-Pro-Asn-Gly-Thr-Phe-Val-Ala-Pro-Arg-Val (TM-MIR2) (SEQ ID NO: 83)

2. Origin Type: Curculin
Structure:
Tyr-Gly-Pro-Val-Leu-Trp-Ser-Leu-Gly-Pro-Asn-Gly (TM-CUR1) (SEQ ID NO: 84)

Macrophage Activating Peptide

Origin Type: Interferon gamma
Applications: The following peptide should activate macrophages for tumor cytotoxicity and to kill parasites. It should be useful in treatment of malaria and other parasitic diseases.
Mechanism: Bind to specific receptors on macrophage surface.
Dose: 10–500 nM.
Administration: Intravenous injections, in situ injections, inhalation, oral administration using coated polymers, dermal patches and other appropriate means.
Structure: Ser-Pro-Ala-Ala-Lys-Thr-Pro-Lys-Arg (IFNG1) (SEQ ID NO: 85)

Anti-contraction Peptides

Application: To prevent premature labor in pregnant women.
Origin Type: Relaxin
Mechanism: Bind to relaxin receptors and induce uterine relaxation.
Dose: 1–20 nmole/mouse
Administration: Intravenous injections, in situ injections, inhalation, oral administration using coated polymers, dermal patches and other appropriate means.

Structures:
Leu-Pro-Gly-Arg-Glu-Leu-Val-Arg-Ala-Gln-Ile-Ala-Ile-Pro-Gly (ACP-R1) (SEQ ID NO: 86)
Leu-Pro-Gly-Arg-Glu-Leu-Val-Arg-Ala-Val-Ile-Gln-Ile-Pro-Gly (ACP-RA) (SEQ ID NO: 87)
Homology: The ACP-R1 and ACP-RA polypeptides have the generalized formula (SEQ ID NO: 150) b-Pro-g-a-d-b-b-a-g based on the conservative substitution groups discussed above.

Antitumor Peptides

Mechanism: Interact with specific receptors and inhibit tumor growth.
Dose: 0.5–10 nM.
Administration: Intravenous injections, in situ injections, inhalation, oral administration using coated polymers, dermal patches or other suitable means.

1. Origin Type: Oncostatin X
Structures:
Asp-Pro-Tyr-Ile-Arg-Ile-Gln-Gly-Leu-Asp-Val-Pro-Lys-Leu (ATP-OSM1) (SEQ ID NO: 88)
Glu-Arg-Pro-Gly-Ala-Phe-Pro-Ser-Glu (ATP-OSM2) (SEQ ID NO: 89)
Glu-Pro-Thr-Lys-Ala-Gly-Arg-Gly-Ala-Ser-Gln-Pro-Ala (ATP-OSM3) (SEQ ID NO: 90)

2. Origin Type: Leukemia Inhibitory Factor
Structures:
Thr-Pro-Val-Asn-Ala-Thr-Pro-Ala (ATP-LIF1) (SEQ ID NO: 91)
Thr-Pro-Ala-Ile-Arg-His-Pro-Ala (ATP-LIF2) (SEQ ID NO: 92)
Phe-Pro-Asn-Asn-Leu-Asp-Lys-Leu-Pro-Gly (ATP-LIF3) (SEQ ID NO: 93)
Gly-Pro-Asn-Val-Thr-Asp-Phe-Pro-Ser (ATP-LIF4) (SEQ ID NO: 94)

Antiplatelet Peptides

1. Origin Type: Leech Antiplatelet Protein
Mechanism: Interacts with collagen receptor and inhibits collagen-induced platelet aggregation.
Dose: 1–4 $\mu$M.
Administration: Intravenous injections, in situ injections, local applications, inhalation, oral administration using coated polymers, dermal patches.
Structures:
Lys-Arg-Pro-Gly-Trp-Lys-Leu-Pro-Asp-Asn (APCol-1) (SEQ ID NO: 95)
Met-Pro-Glu-Glu-Ser-Ala-Val-Glu-Pro-Ser (APCol-2) (SEQ ID NO: 96)

2. Origin Type: Moubatin
Mechanism: Interacts with collagen receptor and inhibits collagen-induced platelet aggregation.
Dose: 1–4 $\mu$M.
Administration: Intravenous injections, in situ injections, local applications, inhalation, oral administration using coated polymers, dermal patches or other appropriate means.
Structures:
Asp-Pro-Gln-Ala-Arg-Asp-Pro-Leu-Lys-Gly-Thr-Pro-Asn (APCol-M1) (SEQ ID NO: 97)
Thr-Pro-Asn-Gly-Asn-Arg-Asp-Gly-Asn-Thr-Leu-Pro-Val (APCol-M2) (SEQ ID NO: 98)

Anti-fibrinogen Peptides

Origin Type: Monoclonal Antibody against the Fibrinogen α chain

Mechanism: Interferes with fibrin polymerization

Dose: 1–2 mM.

Administration: Intravenous injections, in situ injections, local applications, inhalation, oral administration using coated polymers, dermal patches and other appropriate means.

Structure:

His-Pro-Gly-Ile-Ala-Glu-Phe-Pro-Ser-Arg-Ala (AC-9E9) (SEQ ID NO: 99)

Alzheimer's Disease-HGIF

Applications: The brain of Alzheimer's disease patients contains reduced amounts of a growth inhibitory factor (GIF) which is abundant in normal human brain. This may account for the increased neurotrophic activity, leading to massive sprouting of cortical neurons, cell exhaustion and death. The following peptide should replace GIF and hence prevent the development of the disease.

Origin Type: Human Growth Inhibitory Factor

Dose: 1–5000 nM.

Administration: Intravenous injections, in situ injections, local applications, inhalation, oral administration using coated polymers, dermal patches and other appropriate means.

Structure:

Ala-Pro-Ser-Gly-Gly-Ser-Pro-Thr (ADP-GIF1) (SEQ ID NO: 100)

EXAMPLE III

Truncated Analogs as Antagonists or Inhibitors

The following analogs can function as antagonists or inhibitors of natural polypeptides by binding to the natural polypeptide or by competing with the natural polypeptides for their interaction partner(s). These analogs are shorter than their natural counterparts and, thus, are truncated analogs.

Antifertility Peptides

Applications: In population control as a reversible anti-fertility measure.

Origin Type: THR Receptor

Dose: 5–5000 μM

Mechanism: Bind to gonadotropin releasing hormone and thus interfere with the fertility of men and women.

Administration: Intravenous injections, inhalation, oral administration using coated polymers, dermal patches and other appropriate means.

Structures:

Ile-Pro-Leu-Met-Gln-Gly-Asn-Leu-Pro-Thr (AFP-LHRHR1) (SEQ ID NO: 101)

Asp-Pro-Glu-Met-Leu-Asn-Arg-Leu-Ser-Asp-Pro-Val (AFP-LHRHR2) (SEQ ID NO: 102)

Leu-Pro-Thr-Leu-Thr-Leu-Ser-Pro-Lys (AFP-LHRHR3) (SEQ ID NO: 103)

Anti-contraction Peptides

Application: To prevent premature labor in pregnant women.

Origin Type: Angiotensin II Receptor (type 1)

Mechanism: Interact with angiotensin II and abrogate its ability to induce contraction.

Dose: 1–200 μM.

Administration: Intravenous injections, in situ injections, inhalation, oral administration using coated polymers, dermal patches and other appropriate means.

Structures:

Asp-Pro-Ile-Lys-Arg-Ile-Gln-Asp-Asp-Ala-Pro-Lys-Ala (ACP-AT1RA) (SEQ ID NO: 104)

Val-Pro-Ala-Phe-His-Tyr-Glu-Ser-Gln-Asn-Ser-Thr-Leu-Pro-Ile (ACP-AT1RB) (SEQ ID NO: 105)

Trp-Pro-Phe-Gly-Asn-Val-Leu-Pro-Lys (ACP-AT1RC) (SEQ ID NO: 106)

Anti-inflammatory Peptides

1. Origin Type: Interleukin-8 receptor

Mechanism: Bind to interleukin-8 and inhibit its ability to act as a chemo-attractant, and thus abrogate the pro-inflammatory effects of the interleukin.

Dose: 5–50 nM.

Administration: Intravenous injections, in situ injections, inhalation, oral administration using coated polymers, dermal patches and other appropriate means.

Structures:

Leu-Pro-Pro-Phe-Leu-Leu-Asp-Ala-Ala-Pro-Ala (AIP-IL8R1) (SEQ ID NO: 107)

Glu-Pro-Glu-Ser-Leu-Glu-Ile-Asn-Lys-Pro-Tyr (AIP-IL8R2) (SEQ ID NO: 108)

2. Origin Type: Macrophage migration inhibitors

Mechanism: Interacts with specific receptors and inhibits the migration of macrophages, thus stopping pro-inflammatory response.

Dose: 5–100 nM.

Administration: Intravenous injections, in situ injections, inhalation, oral administration using coated polymers, dermal patches and other appropriate means.

Structure:

Lys-Pro-Pro-Gln-Tyr-Ile-Ala-Val-His-Val-Val-Pro-Asp-Gln (AIP-MIF1) (SEQ ID NO: 109)

3. Origin Type: Fibrinogen γ-chain

Mechanism: Inhibits the interactions between fibrinogen and its leukocyte receptor CD11b/CD18 integrin (Mac-1).

Dose: 0.8–20 μM.

Administration: Intravenous injections, in situ injections, inhalation, oral administration using coated polymers, dermal patches and other appropriate means.

Structure:

Asn-Pro-Trp-Thr-Val-Phe-Gln-Lys-Arg-Leu-Asp-Pro-Ser-Val (AIP-FBG1) (SEQ ID NO: 110)

Platelet Derived Growth Factor Inhibitors

Origin Type: Platelet-Derived Growth Factor

Mechanism: Blocks binding of platelet-derived growth factor (PDGF) to its receptor, which blocks the effects of PDGF on smooth muscle.

Dose: 5–5000 μM.

Administration: Intravenous injections, in situ injections, inhalation, oral administration using coated polymers, dermal patches and other appropriate means.

Structures:
Pro-Ser-Gly-Ser-Ala-Pro (PGF-1) (SEQ ID NO: 111)
Pro-Arg-Val-Thr-Asp-Pro (PGF-2) (SEQ ID NO: 112)
Pro-Arg-Gly-Arg-Gly-Met-Pro-Gln-Pro (PGF-3) (SEQ ID NO: 113)

Blood Protein Inhibitors and Antagonists

1. Origin Type: Factor V
    Structures:
    Glu-Met-Lys-Ala-Ser-Lys-Pro-Gly-Trp-Trp-Leu (AC-5A1) (SEQ ID NO: 114)
    Leu-Pro-Gly-Ser-Phe-Lys-Thr-Leu-Glu-Met-Lys-Ala-Ser-Lys-Pro-Gly (AC-5A2) (SEQ ID NO: 115)
    Mechanism: Interferes with the generation of thrombin from prothrombin.
    Dose: 1–2 mM
    Administration: Intravenous injections, in situ injections, local applications, inhalation, oral administration using coated polymers, dermal patches and other appropriate means.
2. Origin Type: Factor VIII
    Mechanism: Interferes with the activation of factor X
    Dose: 1–2 mM
    Administration: Intravenous injections, in situ injections, local applications, inhalation, oral administration using coated polymers, dermal patches and other appropriate means.
    Structures:
    Glu-Met-Leu-Pro-Ser-Lys-Ala-Gly-Ile-Trp-Arg (AC-8A1) (SEQ ID NO: 116)
    Tyr-Pro-Gly-Val-Phe-Glu-Thr-Val-Glu-Met-Leu-Pro-Ser (AC-8A2) (SEQ ID NO: 117)
3. Origin Type: *Naja nigricollis* phospholipase CM-IV
    Mechanism: Interferes with coagulation
    Dose: 1–2 mM
    Administration: Intravenous injections, in situ injections, local applications, inhalation, oral administration using coated polymers, dermal patches and other appropriate means.
    Structures:
    Tyr-Glu-Lys-Ala-Gly-Lys-Met-Gly-Ala-Trp-Pro-Tyr (AC-PL1) (SEQ ID NO: 118)
    Trp-Pro-Tyr-Leu-Thr-Leu-Tyr-Lys-Tyr-Lys-Ala-Ser-Ala (AC-PL2) (SEQ ID NO: 119)
4. Origin Type: Prothrombin
    Mechanism: The native polypeptide, also known as factor II, is the precursor of thrombin. The truncated analog binds with factors that would otherwise generate thrombin from prothrombin.
    Dose: 50–5000 μM.
    Administration: Intravenous injections, in situ injections, local applications, inhalation, oral administration using coated polymers, dermal patches and other appropriate means.
    Structures:
    Ser-Pro-Trp-Gln-Val-Met-Leu-Phe-Arg-Lys-Ser-Pro-Gln-Glu-Leu-Leu-Pro-Gly (ACS-THR1) (SEQ ID NO: 120)
    Leu-Pro-Arg-Lys-Ser-Pro-Gln-Glu-Leu-Leu-Pro-Gly (ACS-THR2) (SEQ ID NO: 121)
    Ile-Pro-Lys-His-Ser-Arg-Thr-Arg-Tyr-Pro-Arg-Asn-Ile-Glu-Lys (ACS-THR3) (SEQ ID NO: 122)
    Homology: The ACS-THR1 and ACS-THR2 polypeptides have the generalized formula (SEQ ID NO:151) a-a-f-Pro-e-d-b-b-Pro-g based on the conservative substitution groups discussed above.
5. Origin Type: Factor Xa
    Mechanism: Interferes in the generation of thrombin from prothrombin.
    Dose: 50–5000 μM.
    Administration: Intravenous injections, in situ injections, local applications, inhalation, oral administration using coated polymers, dermal patches or other appropriate means.
    Structures:
    Ala-Pro-Trp-Gln-Ala-Leu-Leu-Ile-Asn-Glu-Glu-Asn-Glu-Gly-Phe-Pro-Gly (ACS-Xa1) (SEQ ID NO: 123)
    Leu-Pro-Asn-Glu-Glu-Asn-Glu-Gly-Phe-Pro-Gly (ACS-Xa2) (SEQ ID NO: 124)
    Leu-Pro-Asn-Glu-Glu-Asn-Glu-Pro-Phe (ACS-Xa3) (SEQ ID NO: 125)
    Val-Pro-Asp-Arg-Asn-Thr-Glu-Gln-Glu-Glu-Pro-Gly (ACS-Xa4) (SEQ ID NO: 126)
    Homology: The ACS-Xa2 and ACS-Xa3 polypeptides have the generalized formula (SEQ ID NO: 152) b-Pro-e-d-d-e-d based on the conservative substitution groups discussed above.
6. Origin Type: Factor IXa
    Mechanism: Interferes with the activation of factor X
    Dose: 50–5000 μM.
    Administration: Intravenous injections, in situ injections, local applications, inhalation, oral administration using coated polymers, dermal patches and other appropriate means.
    Structure:
    Phe-Pro-Trp-Gln-Val-Val-Leu-Asn-Gly-Lys-Val-Asp-Ala-Phe-Pro-Gly (ACS-IXa1) (SEQ ID NO: 127)
    Asn-Pro-Lys-Val-Asp-Ala-Phe-Pro-Gly (ACS-IXa2) (SEQ ID NO: 128)
    Ala-Pro-Glu-His-Asn-Ile-Glu-Glu-Thr-Glu-His-Thr-Glu-Pro-Lys (ACS-IXa3) (SEQ ID NO: 129)
7. Origin Type: Factor VIIa
    Mechanism: Interferes with the activation of factor X
    Dose: 50–5000 μM.
    Administration: Intravenous injections, in situ injections, local applications, inhalation, oral administration using coated polymers, dermal patches and other appropriate means.
    Structures:
    Ala-Pro-Trp-Gln-Val-Leu-Leu-Leu-Val-Asn-Gly-Ala-Gln-Leu-Pro-Gly (ACS-VIIa1) (SEQ ID NO: 130)
    Ala-Pro-Trp-Gln-Val-Leu-Leu-Leu-Val-Asn-Pro-Ala-Gln-Leu-Pro-Gly (ACS-VIIa2) (SEQ ID NO: 131)
    Leu-Pro-Glu-His-Asp-Leu-Ser-Glu-His-Asp-Pro-Asp (ACS-VIIa3) (SEQ ID NO: 132)
    Homology: The ACS-VIIa1 and ACS-VIIa2 polypeptides have the generalized formula (SEQ ID NO: 153) g-Pro-c-e-b-b-b-b-b-e based on the conservative substitution groups discussed above.

Antiplatelet Peptides
    Several blood proteins are useful for their antiplatelet properties. The proteins can be used as antithrombotic drugs for the prevention and treatment of myocardial infarction, stroke and other related disorders. These proteins may have significant antitumor effects, as well as being useful for wound healing.
1. Origin Type: von Willebrand Factor
    Structure: Ala-Pro-Leu-His-Asp-Phe-Tyr-Pro-Ser (AAP-VWF1) (SEQ ID NO: 133)
    Mechanism: Interferes in the interaction between von Willebrand factor and glycoprotein Ib and thus inhibits platelet agglutination.

Dose: 10–50 μM.

Administration: Intravenous injections, in situ injections, local applications, inhalation, oral administration using coated polymers, dermal patches and other appropriate means.

2. Origin Type: Platelet Glycoprotain IIb

Structure: Gln-Pro-Asn-Asp-Gly-Gln-Pro-His (AAP-GPIIb1) (SEQ ID NO: 134)

Mechanism: Interferes in the interaction of glycoprotein IIb with adhesive ligands.

Dose: 5–100 μM.

Administration: Intravenous injections, in situ injections, local applications, inhalation, oral administration using coated polymers, dermal patches and other appropriate means.

EXAMPLE IV

Homologs

Polypeptide homologs can be based upon biologically active polypeptides, such as naturally-occurring polypeptides or polypeptides derived therefrom, which do not contain conformation-constraining moieties, such as proline, around interaction sites. Such polypeptides can be altered by inserting conformation-constraining moieties into the polypeptide so that these moieties bracket the interaction site.

Homologs of polypeptides that already contain conformation-constraining brackets also can be made, according to the present invention, by altering the location or structure of the bracket. For instance, a naturally-occurring proline residue that is within five amino acids of an interaction site can be moved to be within two amino acids of the interaction site. Additionally, a cyclic constraining moiety can be substituted with a proline to alter the properties of the interaction site. Furthermore, as stated above a homolog can also be shortened so that its length is less than that of the native polypeptide. These and other changes will become apparent in view of the teachings of this application.

Like the analogs, homologs can mimic the activity of the native polypeptide or serve as antagonists. The non-limiting examples below include mimicking and antagonizing homologs. The sequences of the native polypeptides are known.

Analgesics

Origin Type: Enkephalins

Application: Alleviation of pain and emotional stress.

Dose: 5–5000 μM.

Administration: Intravenous injections, in situ injections, inhalation, oral administration with coated polymers, dermal patches, and other appropriate means.

Structures:

Pro-Tyr-Gly-Gly-Phe-Met-Pro (AN-1) (SEQ ID NO: 135)

Pro-Tyr-Gly-Gly-Phe-Leu-Pro (AN-2) (SEQ ID NO: 136)

Appetite Suppressant

Origin Type: Cholecystokinin

Application: Suppression of appetite.

Administration: Intravenous injections, in situ injections, inhalation, oral administration with coated polymers, dermal patches, and other appropriate means.

Dose: 5–5000 μM.

Structure:

Pro-Phe(4-tetrazole)-Met-Gly-Trp-Met-Asp-Phe-Pro (AS-1) (SEQ ID NO: 137)

B-Cell Differentiating Peptide

Origin Type: B-Cell Differentiating Peptide

Application: Treatment of immune disorders resulting from low levels of gamma globulin Administration: Intravenous injections, in situ injections, inhalation, oral administration with coated polymers, dermal patches, and other appropriate means.

Dose: 5–5000 μM.

Structure:

Pro-Lys-His-Gly-Pro (BCD-1) (SEQ ID NO: 138)

Hypocalcemic Agent

Origin Type: Calcitonin

Application: Mimics human calcitonin. Lowers blood calcium and phosphate levels, and prevents demineralization of bones.

Administration: Intravenous injections, in situ injections, inhalation, oral administration with coated polymers, dermal patches, and other appropriate means.

Dose: 5–5000 μM.

Structure:

Pro-Gln-Thr-Ala-Ile-Gly-Val-Gly-Ala-Pro (HCA-1) (SEQ ID NO: 139)

Hypoglycemic Potentiator

Origin Type: Human Growth Hormone

Application: Useful for lowering the effective dosages of insulin.

Administration: Intravenous injections, in situ injections, inhalation, oral administration with coated polymers, dermal patches, and other appropriate means.

Dose: 5–5000 μM.

Structure:

Pro-Glu-Glu-Ala-Tyr-Ile-Pro-Lys (HGP-1) (SEQ ID NO: 140)

Hypotensive Agent

Origin Type: Prolyl-phenylalanyl-arginine chains

Application: Reduction of blood pressure by reducing kidney vessel resistance.

Administration: Intravenous injections, in situ injections, inhalation, oral administration with coated polymers, dermal patches, and other appropriate means.

Dose: 5–5000 μM.

Structure:

Pro-Pro-Phe-Arg-Pro (HTA-1) (SEQ ID NO: 141)

Immune Potentiator

Application: Stimulates differentiation of stem cells into thymus-derived cells and antibody production.

Administration: Intravenous injections, in situ injections, inhalation, oral administration with coated polymers, dermal patches, and other appropriate means.

Dose: 5–5000 μM.

1. Origin Type: Thymopoietin

Structure:

Arg-Pro-Asp-Gly-Trp-Pro (IP-1) (SEQ ID NO: 142)

2. Origin Type: Thymosin α1

Structure:

Pro-Val-Glu-Glu-Ala-Glu-Asn-Pro (IP-2) (SEQ ID NO: 143)

Somatostatin-like Peptide

Origin Type: Type: Somatostatin

Application: To inhibit oversecretion of glucagon and/or growth hormone in conditions such as acromegaly and diabetes.

Administration: Intravenous injections, in situ injections.. inhalation, oral administration with coated polymers, dermal patches, and other appropriate means.

Dose: 5–5000 μM.

Structure:

Pro-Lys-Asn-Phe-Phe-Trp-Lys-Thr-Phe-Thr-Pro (SLP-1) (SEQ ID NO: 144)

Gastrin-releasing Peptide Antagonists

Origin Type: Gastrin Releasing Peptide

Application: Inhibits the action of gastrin-releasing peptide. Can be used for treatment of small cell lung carcinoma by prevention of the growth-promoting action of gastrin-releasing peptide.

Administration: Intravenous injections, in situ injections, inhalation, oral administration with coated polymers, dermal patches, and other appropriate means.

Dose: 5–5000 μM.

Structure:

Pro-His-Trp-Ala-Val-Gly-His-Leu-Pro (GRP-1) (SEQ ID NO: 145)

The foregoing description, specific examples and data, while indicating preferred embodiments, are given by way of illustration and are not intended to limit the present invention. Various changes and modifications within the present invention will be apparent to the skilled artisan from the discussion and disclosure contained herein.

---

What is claimed is:

1. A method of obtaining a putative protein-protein interaction site of a biologically-active polypeptide, comprising (A) searching the polypeptide for a region of no more than 30 amino acids that is flanked on each termini by at least one proline residue; and (B) isolating or producing the flanked region.

2. The method according to claim 1, the flanked region comprises no more than 25 amino acid residues.

3. The method according to claim 1, wherein the flanked region comprises no more than 15 amino acid residues.

4. The method according to claim 1, wherein (B) comprises producing the putative protein-protein interaction site by peptide synthesis.

5. A method of obtaining a putative protein-protein interaction site of a biologically-active polypeptide, comprising (A) searching the polypeptide for a region of no more than 30 amino acids that is flanked on each termini by at least one proline residue;

(B) identifying the flanked region; and (C) producing the flanked region by peptide synthesis.

6. The method according to claim 5, wherein the producing is performed via solid phase synthesis.

7. The method according to claim 5, wherein the producing is performed via solution phase synthesis.

8. The method according to claim 5, wherein the producing introduces a D-amino acid.

9. The method according to claim 5, wherein the producing introduces an L-amino acid.

* * * * *

SEQUENCE LISTING (1) GENERAL INFORMATION:

(iii) NUMBER OF SEQUENCES: 153

(2) INFORMATION FOR SEQ ID NO: 1:

(i) SEQUENCE CHARACTERISTICS:
      (A) LENGTH: 3 amino acids
      (B) TYPE: amino acid
      (D) TOPOLOGY: linear (xi) SEQUENCE DESCRIPTION: SEQ ID NO: 1:

Arg Gly Asp
1

(2) INFORMATION FOR SEQ ID NO: 2:

(i) SEQUENCE CHARACTERISTICS:
      (A) LENGTH: 8 amino acids
      (B) TYPE: amino acid
      (D) TOPOLOGY: linear (xi) SEQUENCE DESCRIPTION: SEQ ID NO: 2:

Ile Ala Arg Gly Asp Met Asn Ala
1         5

(2) INFORMATION FOR SEQ ID NO: 3:

(i) SEQUENCE CHARACTERISTICS:
      (A) LENGTH: 8 amino acids
      (B) TYPE: amino acid
      (D) TOPOLOGY: linear (xi) SEQUENCE DESCRIPTION: SEQ ID NO: 3:

Ile Pro Arg Gly Asp Met Asn Ala
1         5

(2) INFORMATION FOR SEQ ID NO: 4:

(i) SEQUENCE CHARACTERISTICS:
      (A) LENGTH: 8 amino acids
      (B) TYPE: amino acid
      (D) TOPOLOGY: linear (xi) SEQUENCE DESCRIPTION: SEQ ID NO: 4:

Ile Ala Arg Gly Asp Met Pro Ala
1               5

(2) INFORMATION FOR SEQ ID NO: 5:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO: 5:

Ile Pro Arg Gly Asp Met Pro Ala
1               5

(2) INFORMATION FOR SEQ ID NO: 6:

(i) SEQUENCE CHARACTERISTICS:
            (A) LENGTH: 4 amino acids
            (B) TYPE: amino acid
            (D) TOPOLOGY: linear (xi) SEQUENCE DESCRIPTION: SEQ ID NO: 6:

Arg Gly Asp Ser
1

(2) INFORMATIO N FOR SEQ ID NO:7:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO: 7:

Ile Pro Arg Gly Asp Tyr Pro Ala
1               5

(2) INFORMATION FOR SEQ ID NO: 8:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO: 8:

Ile Pro Arg Gly Asp Phe Pro Ala
1               5

(2) INFORMATION FOR SEQ ID NO: 9:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO: 9:

Ile Pro Arg Gly Asp Trp Pro Ala
1               5

(2) INFORMATION FOR SEQ ID NO: 10:

(i) SEQUENCE CHARACTERISTICS:
            (A) LENGTH: 8 amino acids
            (B) TYPE: amino acid
            (D) TOPOLOGY: linear

```
    (xi) SEQUENCE DESCRIPTION: SEQ ID NO: 10:

Ile Pro Lys Gly Asp Trp Pro Ala
1               5

(2) INFORMATION FOR SEQ ID NO: 11:

(i) SEQUENCE CHARACTERISTICS:
        (A) LENGTH: 8 amino acids
        (B) TYPE: amino acid
        (D) TOPOLOGY: linear (ix) FEATURE:
        (A) NAME/KEY: Modified-site
        (B) LOCATION: 3
        (D) OTHER INFORMATION: /note= "Arg at position 3
            represents homoarginine"

(xi) SEQUENCE DESCRIPTION: SEQ ID NO: 11:

Ile Pro Arg Gly Asp Trp Pro Ala
1               5

(2) INFORMATION FOR SEQ ID NO: 12:

(i) SEQUENCE CHARACTERISTICS:
        (A) LENGTH: 3 amino acids
        (B) TYPE: amino acid
        (D) TOPOLOGY: linear (xi) SEQUENCE DESCRIPTION: SEQ ID NO: 12:

Leu Asp Val
1

(2) INFORMATION FOR SEQ ID NO: 13:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 13:

Ala Pro Leu Asp Val Pro Ala
1               5

(2) INFORMATION FOR SEQ ID NO: 14:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO: 14:

Val Thr Cys Gly
1

(2) INFORMATION FOR SEQ ID NO: 15:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 15:

Ala Pro Val Thr Cys Gly Pro Ala
1               5
```

(2) INFORMATION FOR SEQ ID NO: 16:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 16:

Ala Pro Thr Ala Met Trp Pro Ala
1               5

(2) INFORMATION FOR SEQ ID NO: 17:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 17:

Ala Pro Arg Ser Lys Ile Ser Pro Gln Gly
1               5                   10

(2) INFORMATION FOR SEQ ID NO: 18:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 18:

Gln Leu Pro Gly Asn Ser Val Phe Lys Glu Pro Met
1               5                   10

(2) INFORMATION FOR SEQ ID NO: 19:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 19:

Phe Thr Ser Met Asp Thr Ser Gln Leu Pro Gly
1               5                   10

(2) INFORMATION FOR SEQ ID NO: 20:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 20:

Ser Pro Arg Tyr Val Glu Phe Pro Ile Lys Pro Gly
1               5                   10

(2) INFORMATION FOR SEQ ID NO: 21:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 21:

Phe Pro Ile Thr Glu Lys Gly Phe Val Val Pro Asp
1               5                   10

(2) INFORMATION FOR SEQ ID NO: 22:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 22:

```
Val Pro Asp Leu Ser Glu His Ile Lys Asn Pro Gly
1               5                   10
```

(2) INFORMATION FOR SEQ ID NO: 23:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 23:

```
Lys Pro Asp Asp Ala Ser Tyr Phe Glu Pro Thr Gly Pro Tyr
1               5                   10
```

(2) INFORMATION FOR SEQ ID NO: 24:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 24:

```
Arg Pro Tyr Lys Glu Lys Pro Val
1               5
```

(2) INFORMATION FOR SEQ ID NO: 25:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 25:

```
Thr Pro Leu Asn Pro Asp Asp Phe Arg Pro Gly
1               5                   10
```

(2) INFORMATION FOR SEQ ID NO: 26:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 26:

```
Ser Pro Lys Ser Lys Pro Phe Ala Thr Asp Ser Gly Ala Met Pro His
1               5                   10                  15
```

(2) INFORMATION FOR SEQ ID NO: 27:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 27:

```
Ala Pro Gln Phe Val Gln Asn Ile Pro Ala
1               5                   10
```

(2) INFORMATION FOR SEQ ID NO: 28:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 28:

```
Lys Glu Leu Arg Pro Gln
1               5
```

(2) INFORMATION FOR SEQ ID NO: 29:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 29:

```
Ala Pro Glu Val Lys Phe Asn Lys Pro Phe Val
1               5                   10
```

(2) INFORMATION FOR SEQ ID NO: 30:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 30:

```
Ser Pro Leu Phe Ile Gly Lys Val Val Asn Pro Thr
1               5                   10
```

(2) INFORMATION FOR SEQ ID NO: 31:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 31:

```
Ser Lys Pro Ala Gly Lys Leu Thr Lys Ser Lys Pro Gln Ala
1               5                   10
```

(2) INFORMATION FOR SEQ ID NO: 32:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 32:

```
Ser Lys Pro Ala Gly Lys Leu Thr Lys Pro Lys Pro Gln Ala
1               5                   10
```

(2) INFORMATION FOR SEQ ID NO: 33:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 33:

```
Lys Ile Pro Ala Asn Trp Lys Lys Gln Phe Pro Ala
1               5                   10
```

(2) INFORMATION FOR SEQ ID NO: 34:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 34:

```
Val Pro Val Ala Ser Thr Asp Arg Trp Ser Glu Leu Thr Glu Ala
1               5                   10                  15
```

(2) INFORMATION FOR SEQ ID NO: 35:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 35:

```
Ile Pro Arg Asn Glu Ala Asp Gly Met Pro Ile
1               5                   10
```

(2) INFORMATION FOR SEQ ID NO: 36:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 36:

```
Ala Pro Ser Gln Ala Leu Gln Leu Ala Pro Ala
1               5                   10
```

(2) INFORMATION FOR SEQ ID NO: 37:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 37:

```
Ala Pro Ala Leu Gln Pro Thr Gln Gly Ala Met Pro Ala
1               5                   10
```

(2) INFORMATION FOR SEQ ID NO: 38:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 38:

```
Ile Pro Trp Ala Pro Leu Ser Ser Ala Pro Ser
1               5                   10
```

(2) INFORMATION FOR SEQ ID NO: 39:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 39:

```
Ser Pro Glu Leu Gly Pro Thr Leu
1               5
```

(2) INFORMATION FOR SEQ ID NO: 40:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 40:

```
Thr Pro Leu Gly Pro Ala Ser Ser Leu Pro Gln Ser
1               5                   10
```

(2) INFORMATION FOR SEQ ID NO: 41:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 41:

```
Leu Pro Leu Ala Thr Ala Ala Pro Thr Arg His Pro Ile
1               5                   10
```

(2) INFORMATION FOR SEQ ID NO: 42:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 42:

```
Asp Pro Val Val Ser Ser Thr Leu Ser Pro Glu
1               5                   10
```

(2) INFORMATION FOR SEQ ID NO: 43:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 43:

```
Val Pro Gly Met Asp Val Leu Pro Ser
1               5
```

(2) INFORMATION FOR SEQ ID NO: 44:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 44:

```
Ser Pro Glu Pro Arg Leu Phe Thr Pro Glu
1               5                   10
```

(2) INFORMATION FOR SEQ ID NO: 45:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 45:

```
Tyr Pro Asp Glu Ile Glu Tyr Ile Phe Lys Pro Ser
1               5                   10
```

(2) INFORMATION FOR SEQ ID NO: 46:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 46:

```
Ser Pro Asp Lys Gln Ala Ala Ala Leu Pro Arg Arg
1               5                   10
```

(2) INFORMATION FOR SEQ ID NO: 47:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 47:

```
Asn Pro Glu Asn Ser Arg Pro Lys
1               5
```

(2) INFORMATION FOR SEQ ID NO: 48:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 48:

```
Thr Pro Ala Leu Phe Pro Lys
1               5
```

(2) INFORMATION FOR SEQ ID NO: 49:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 49:

```
Asn Pro Ala Gly Trp Thr Gly Asn Pro Asn
1               5                   10
```

(2) INFORMATION FOR SEQ ID NO: 50:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 50:

```
Ala Pro Ile Tyr Asn Ala Asp Glu Leu Ile Pro Arg
1               5                   10
```

(2) INFORMATION FOR SEQ ID NO: 51:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 51:

```
Tyr Thr Pro Asn Trp Gly Arg Gly Asn Pro Asn Asn
1               5                   10
```

(2) INFORMATION FOR SEQ ID NO: 52:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 52:

```
Gly Asn Pro Asn Asn Phe Ile Asp Thr Val Thr Phe Pro Lys Val
1               5                   10                  15
```

(2) INFORMATION FOR SEQ ID NO: 53:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 53:

```
Leu Pro Val Thr Asp Ile Phe Ala Ala Pro Lys
1               5                   10
```

(2) INFORMATION FOR SEQ ID NO: 54:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 54:

```
Ala Pro Val Lys Glu Ala Asn Gln Pro Thr
1               5                   10
```

(2) INFORMATION FOR SEQ ID NO: 55:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 55:

```
Thr Pro Ala Thr Glu Leu Thr Val Pro Asp
1               5                   10
```

(2) INFORMATION FOR SEQ ID NO: 56:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 56:

```
Ser Pro His Glu Lys Asp Thr Arg Pro Leu
1               5                   10
```

(2) INFORMATION FOR SEQ ID NO: 57:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 57:

```
Val Pro Gln Ala Glu Asn Gln Asp Pro Asp Ile
1               5                   10
```

(2) INFORMATION FOR SEQ ID NO: 58:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 58:

```
Arg Pro His Arg Phe Leu Pro Ala
1               5
```

(2) INFORMATION FOR SEQ ID NO: 59:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 59:

```
His Phe Pro Gly Asn Leu Pro Asn Met Leu
1               5                   10
```

(2) INFORMATION FOR SEQ ID NO: 60:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 60:

```
Thr Pro Ala Ile Asp Leu Leu Glu Thr Tyr Lys Tyr Gly Asp Pro Ile
1               5                   10                  15
```

(2) INFORMATION FOR SEQ ID NO: 61:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 61:

```
Asp Pro Ile Tyr Lys Glu Ala Lys Asp Arg Leu Met Thr Arg
1               5                   10
```

(2) INFORMATION FOR SEQ ID NO: 62:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 62:

```
Asn Pro His Lys Ile Thr Asn Glu Arg Ile Lys
1               5                   10
```

(2) INFORMATION FOR SEQ ID NO: 63:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 63:

```
Glu Leu Arg Ala Lys Leu Asp Leu Ile Leu Pro Asp
1               5                   10
```

(2) INFORMATION FOR SEQ ID NO: 64:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 64:

Ser Pro Val Val Lys Glu Glu Asn Lys Val Glu Glu Pro Gln Leu
1               5                   10                  15

(2) INFORMATION FOR SEQ ID NO: 65:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 65:

Lys Pro Thr Asn Asn Lys Trp Trp Ile Ile Pro Ala
1               5                   10

(2) INFORMATION FOR SEQ ID NO: 66:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 66:

Ala Pro Ser Gly Trp Ser Ser Tyr Glu Gly Asn Pro Tyr
1               5                   10

(2) INFORMATION FOR SEQ ID NO: 67:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 67:

Asn Pro Phe Val Ala Lys Ser Pro Ala
1               5

(2) INFORMATION FOR SEQ ID NO: 68:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 68:

Arg Pro Arg Gly Asn Thr Leu Ser Pro Ala
1               5                   10

(2) INFORMATION FOR SEQ ID NO: 69:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 69:

Gly Pro Ser Val Arg Gly Asn Thr Leu Ser Pro Ala
1               5                   10

```
(2) INFORMATION FOR SEQ ID NO: 70:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 70:

Ala Pro Ala Lys Leu Lys Ala Pro Gly
1               5

(2) INFORMATION FOR SEQ ID NO: 71:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 71:

Ala Pro Gly Ser Ser Asn Tyr Arg Val Thr Phe Ala Pro Thr Ala
1               5                   10                  15

(2) INFORMATION FOR SEQ ID NO: 72:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 72:

Gly Pro Thr Glu Tyr Ser Arg Phe Phe Lys Arg Leu Ala Pro Asp
1               5                   10                  15

(2) INFORMATION FOR SEQ ID NO: 73:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 73:

Asp Lys Pro Thr Thr Val Thr Ala Pro Gly
1               5                   10

(2) INFORMATION FOR SEQ ID NO: 74:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 74:

Asn Val Pro Met Asn Phe Ser Pro Thr Thr
1               5                   10

(2) INFORMATION FOR SEQ ID NO: 75:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 75:

Ile Arg Pro Ala Met Lys Lys Thr Ile Tyr Glu Asn Glu
1               5                   10
```

(2) INFORMATION FOR SEQ ID NO: 76:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 76:

Arg Pro Arg Lys Leu Leu Arg Phe Asn Gly Pro Val
1               5                   10

(2) INFORMATION FOR SEQ ID NO: 77:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 77:

Gln Pro Arg Arg Pro Ala Leu Arg Gln Pro Ala
1               5                   10

(2) INFORMATION FOR SEQ ID NO: 78:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 78:

Ala Pro Asn Gln Leu Arg Gln Val Asp Arg Pro Ala
1               5                   10

(2) INFORMATION FOR SEQ ID NO: 79:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 79:

Ile Pro Asn Ile Gly Ala Ala Pro Phe Arg Ala Trp
1               5                   10

(2) INFORMATION FOR SEQ ID NO: 80:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 80:

Ile His Arg Arg Ala Gln Phe Gly Gly Gln Pro Asp
1               5                   10

(2) INFORMATION FOR SEQ ID NO: 81:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 81:

Leu Pro Asn Ile Ala Asn Ile Pro Asn
1               5

(2) INFORMATION FOR SEQ ID NO: 82:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 82:

```
Asp Arg Pro Leu Ala Phe Phe Pro Glu Asn Pro Lys Glu
1               5                   10
```

(2) INFORMATION FOR SEQ ID NO: 83:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 83:

```
Thr Thr Pro Asn Gly Thr Phe Val Ala Pro Arg Val
1               5                   10
```

(2) INFORMATION FOR SEQ ID NO: 84:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 84:

```
Tyr Gly Pro Val Leu Trp Ser Leu Gly Pro Asn Gly
1               5                   10
```

(2) INFORMATION FOR SEQ ID NO: 85:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 85:

```
Ser Pro Ala Ala Lys Thr Pro Lys Arg
1               5
```

(2) INFORMATION FOR SEQ ID NO: 86:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 86:

```
Leu Pro Gly Arg Glu Leu Val Arg Ala Gln Ile Ala Ile Pro Gly
1               5                   10                  15
```

(2) INFORMATION FOR SEQ ID NO: 87:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 87:

```
Leu Pro Gly Arg Glu Leu Val Arg Ala Val Ile Gln Ile Pro Gly
1               5                   10                  15
```

(2) INFORMATION FOR SEQ ID NO: 88:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 88:

```
Asp Pro Tyr Ile Arg Ile Gln Gly Leu Asp Val Pro Lys Leu
1               5                   10
```

(2) INFORMATION FOR SEQ ID NO: 89:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 89:

```
Glu Arg Pro Gly Ala Phe Pro Ser Glu
1               5
```

(2) INFORMATION FOR SEQ ID NO: 90:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 90:

```
Glu Pro Thr Lys Ala Gly Arg Gly Ala Ser Gln Pro Ala
1               5                   10
```

(2) INFORMATION FOR SEQ ID NO: 91:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 91:

```
Thr Pro Val Asn Ala Thr Pro Ala
1               5
```

(2) INFORMATION FOR SEQ ID NO: 92:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 92:

```
Thr Pro Ala Ile Arg His Pro Ala
1               5
```

(2) INFORMATION FOR SEQ ID NO: 93:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 93:

```
Phe Pro Asn Asn Leu Asp Lys Leu Pro Gly
1               5                   10
```

(2) INFORMATION FOR SEQ ID NO: 94:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 94:

```
Gly Pro Asn Val Thr Asp Phe Pro Ser
1               5
```

(2) INFORMATION FOR SEQ ID NO: 95:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 95:

```
Lys Arg Pro Gly Trp Lys Leu Pro Asp Asn
1               5                   10
```

(2) INFORMATION FOR SEQ ID NO: 96:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 96:

```
Met Pro Glu Glu Ser Ala Val Glu Pro Ser
1               5                   10
```

(2) INFORMATION FOR SEQ ID NO: 97:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 97:

```
Asp Pro Gln Ala Arg Asp Pro Leu Lys Gly Thr Pro Asn
1               5                   10
```

(2) INFORMATION FOR SEQ ID NO: 98:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 98:

```
Thr Pro Asn Gly Asn Arg Asp Gly Asn Thr Leu Pro Val
1               5                   10
```

(2) INFORMATION FOR SEQ ID NO: 99:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 99:

```
His Pro Gly Ile Ala Glu Phe Pro Ser Arg Ala
1               5                   10
```

(2) INFORMATION FOR SEQ ID NO: 100:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 100:

```
Ala Pro Ser Gly Gly Ser Pro Thr
1               5
```

(2) INFORMATION FOR SEQ ID NO: 101:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 101:

```
Ile Pro Leu Met Gln Gly Asn Leu Pro Thr
1               5                   10
```

(2) INFORMATION FOR SEQ ID NO: 102:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 102:

```
Asp Pro Glu Met Leu Asn Arg Leu Ser Asp Pro Val
1               5                   10
```

(2) INFORMATION FOR SEQ ID NO: 103:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 103:

```
Leu Pro Thr Leu Thr Leu Ser Pro Lys
1               5
```

(2) INFORMATION FOR SEQ ID NO: 104:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 104:

```
Asp Pro Ile Lys Arg Ile Gln Asp Asp Ala Pro Lys Ala
1               5                   10
```

(2) INFORMATION FOR SEQ ID NO: 105:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 105:

```
Val Pro Ala Phe His Tyr Glu Ser Gln Asn Ser Thr Leu Pro Ile
1               5                   10                  15
```

```
(2) INFORMATION FOR SEQ ID NO: 106:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 106:

Trp Pro Phe Gly Asn Val Leu Pro Lys
1               5

(2) INFORMATION FOR SEQ ID NO: 107:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 107:

Leu Pro Pro Phe Leu Leu Asp Ala Ala Pro Ala
1               5                   10

(2) INFORMATION FOR SEQ ID NO: 108:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 108:

Glu Pro Glu Ser Leu Glu Ile Asn Lys Pro Tyr
1               5                   10

(2) INFORMATION FOR SEQ ID NO: 109:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 109:

Lys Pro Pro Gln Tyr Ile Ala Val His Val Val Pro Asp Gln
1               5                   10

(2) INFORMATION FOR SEQ ID NO: 110:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 110:

Asn Pro Trp Thr Val Phe Gln Lys Arg Leu Asp Pro Ser Val
1               5                   10

(2) INFORMATION FOR SEQ ID NO: 111:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 111:

Pro Ser Gly Ser Ala Pro
1               5
```

(2) INFORMATION FOR SEQ ID NO: 112:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 112:

```
Pro Arg Val Thr Asp Pro
1               5
```

(2) INFORMATION FOR SEQ ID NO: 113:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 113:

```
Pro Arg Gly Arg Gly Met Pro Gln Pro
1               5
```

(2) INFORMATION FOR SEQ ID NO: 114:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 114:

```
Glu Met Lys Ala Ser Lys Pro Gly Trp Trp Leu
1               5                   10
```

(2) INFORMATION FOR SEQ ID NO: 115:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 115:

```
Leu Pro Gly Ser Phe Lys Thr Leu Glu Met Lys Ala Ser Lys Pro Gly
1               5                   10                  15
```

(2) INFORMATION FOR SEQ ID NO: 116:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 116:

```
Glu Met Leu Pro Ser Lys Ala Gly Ile Trp Arg
1               5                   10
```

(2) INFORMATION FOR SEQ ID NO: 117:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 117:

```
Tyr Pro Gly Val Phe Glu Thr Val Glu Met Leu Pro Ser
1               5                   10
```

(2) INFORMATION FOR SEQ ID NO: 118:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 118:

```
Tyr Glu Lys Ala Gly Lys Met Gly Ala Trp Pro Tyr
1               5                   10
```

(2) INFORMATION FOR SEQ ID NO: 119:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 119:

```
Trp Pro Tyr Leu Thr Leu Tyr Lys Tyr Lys Ala Ser Ala
1               5                   10
```

(2) INFORMATION FOR SEQ ID NO: 120:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO: 120:

```
Ser Pro Trp Gln Val Met Leu Phe Arg Lys Ser Pro Gln Glu Leu Leu
1               5                   10                  15
Pro Gly
```

(2) INFORMATION FOR SEQ ID NO: 121:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 121:

```
Leu Pro Arg Lys Ser Pro Gln Glu Leu Leu Pro Gly
1               5                   10
```

(2) INFORMATION FOR SEQ ID NO: 122:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 122:

```
Ile Pro Lys His Ser Arg Thr Arg Tyr Pro Arg Asn Ile Glu Lys
1               5                   10                  15
```

(2) INFORMATION FOR SEQ ID NO: 123:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO: 123:

```
Ala Pro Trp Gln Ala Leu Leu Ile Asn Glu Glu Asn Glu Gly Phe Pro
1               5                   10                  15
```

Gly (2) INFORMATION FOR SEQ ID NO: 124:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 124:

Leu Pro Asn Glu Glu Asn Glu Gly Phe Pro Gly
1               5                   10

(2) INFORMATION FOR SEQ ID NO: 125:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 125:

Leu Pro Asn Glu Glu Asn Glu Pro Phe
1               5

(2) INFORMATION FOR SEQ ID NO: 126:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 126:

Val Pro Asp Arg Asn Thr Glu Gln Glu Glu Pro Gly
1               5                   10

(2) INFORMATION FOR SEQ ID NO: 127:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 127:

Phe Pro Trp Gln Val Val Leu Asn Gly Lys Val Asp Ala Phe Pro Gly
1               5                   10                  15

(2) INFORMATION FOR SEQ ID NO: 128:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 128:

Asn Pro Lys Val Asp Ala Phe Pro Gly
1               5

(2) INFORMATION FOR SEQ ID NO: 129:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 129:

```
Ala Pro Glu His Asn Ile Glu Glu Thr Glu His Thr Glu Pro Lys
1               5                   10                  15
```

(2) INFORMATION FOR SEQ ID NO: 130:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 130:

```
Ala Pro Trp Gln Val Leu Leu Leu Val Asn Gly Ala Gln Leu Pro Gly
1               5                   10                  15
```

(2) INFORMATION FOR SEQ ID NO: 131:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 131:

```
Ala Pro Trp Gln Val Leu Leu Leu Val Asn Pro Ala Gln Leu Pro Gly
1               5                   10                  15
```

(2) INFORMATION FOR SEQ ID NO: 132:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 132:

```
Leu Pro Glu His Asp Leu Ser Glu His Asp Pro Asp
1               5                   10
```

(2) INFORMATION FOR SEQ ID NO: 133:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 133:

```
Ala Pro Leu His Asp Phe Tyr Pro Ser
1               5
```

(2) INFORMATION FOR SEQ ID NO: 134:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 134:

```
Gln Pro Asn Asp Gly Gln Pro His
1               5
```

(2) INFORMATION FOR SEQ ID NO: 135:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 135:

```
Pro Tyr Gly Gly Phe Met Pro
1               5
```

(2) INFORMATION FOR SEQ ID NO: 136:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 136:

```
Pro Tyr Gly Gly Phe Leu Pro
1               5
```

(2) INFORMATION FOR SEQ ID NO: 137:

(i) SEQUENCE CHARACTERISTICS:
        (A) LENGTH: 9 amino acids
        (B) TYPE: amino acid
        (D) TOPOLOGY: linear (ix) FEATURE:
        (A) NAME/KEY: Modified-site
        (B) LOCATION: 2
        (D) OTHER INFORMATION: /note= "Phe at position 2
            represents Phe(4-tetrazole)"

(xi) SEQUENCE DESCRIPTION: SEQ ID NO: 137:

```
Pro Phe Met Gly Trp Met Asp Phe Pro
1               5
```

(2) INFORMATION FOR SEQ ID NO: 138:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO: 138:

```
Pro Lys His Gly Pro
1               5
```

(2) INFORMATION FOR SEQ ID NO: 139:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 139:

```
Pro Gln Thr Ala Ile Gly Val Gly Ala Pro
1               5                   10
```

(2) INFORMATION FOR SEQ ID NO: 140:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 140:

```
Pro Glu Glu Ala Tyr Ile Pro Lys
1               5
```

(2) INFORMATION FOR SEQ ID NO: 141:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO: 141:

Pro Pro Phe Arg Pro
1          5

(2) INFORMATION FOR SEQ ID NO: 142:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 142:

Arg Pro Asp Gly Trp Pro
1          5

(2) INFORMATION FOR SEQ ID NO: 143:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 143:

Pro Val Glu Glu Ala Glu Asn Pro
1          5

(2) INFORMATION FOR SEQ ID NO: 144:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO: 144:

Pro Lys Asn Phe Phe Trp Lys Thr Phe Thr Pro
1          5              10

(2) INFORMATION FOR SEQ ID NO: 145:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 145:

Pro His Trp Ala Val Gly His Leu Pro
1          5

(2) INFORMATION FOR SEQ ID NO: 146:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Modified-site
        (B) LOCATION: 1
        (D) OTHER INFORMATION: /note= "Xaa at position 1
            represents Leu, Ile, Val, Met or Norleu"

```
        (ix) FEATURE:
              (A) NAME/KEY: Modified-site
              (B) LOCATION: 3
              (D) OTHER INFORMATION: /note= "Xaa at position 3
                  represents Lys, Arg, Homoarg or Orn"

(ix) FEATURE:
              (A) NAME/KEY: Modified-site
              (B) LOCATION: 4
              (D) OTHER INFORMATION: /note= "Xaa at position 4
                  represents Ala or Gly"

(ix) FEATURE:
              (A) NAME/KEY: Modified-site
              (B) LOCATION: 5
              (D) OTHER INFORMATION: /note= "Xaa at position 5
                  represents Glu or Asp"

(ix) FEATURE:
              (A) NAME/KEY: Modified-site
              (B) LOCATION: 6
              (D) OTHER INFORMATION: /note= "Xaa at position 6
                  represents Leu, Ile, Val, Met or Norleu"

(xi) SEQUENCE DESCRIPTION: SEQ ID NO: 146:

Xaa Pro Xaa Xaa Xaa Xaa
1               5

(2) INFORMATION FOR SEQ ID NO: 147:

(i) SEQUENCE CHARACTERISTICS:
              (A) LENGTH: 8 amino acids
              (B) TYPE: amino acid
              (D) TOPOLOGY: linear (ix) FEATURE:
              (A) NAME/KEY: Modified-site
              (B) LOCATION: 1
              (D) OTHER INFORMATION: /note= "Xaa at position 1
                  represents Leu, Ile, Val, Met or Norleu"

(ix) FEATURE:
              (A) NAME/KEY: Modified-site
              (B) LOCATION: 3
              (D) OTHER INFORMATION: /note= "Xaa at position 3
                  represents Lys, Arg, Homoarg or Orn"

(ix) FEATURE:
              (A) NAME/KEY: Modified-site
              (B) LOCATION: 4
              (D) OTHER INFORMATION: /note= "Xaa at position 4
                  represents Ala or Gly"

(ix) FEATURE:
              (A) NAME/KEY: Modified-site
              (B) LOCATION: 5
              (D) OTHER INFORMATION: /note= "Xaa at positions 5
                  represents Glu or Asp"

(ix) FEATURE:
              (A) NAME/KEY: Modified-site
              (B) LOCATION: 6
              (D) OTHER INFORMATION: /note= "Xaa at position 6
                  represents Tyr, Phe or Trp"

(ix) FEATURE:
              (A) NAME/KEY: Modified-site
              (B) LOCATION: 8
              (D) OTHER INFORMATION: /note= "Xaa at position 8
                  represents Ala or Gly"

(xi) SEQUENCE DESCRIPTION: SEQ ID NO: 147:

Xaa Pro Xaa Xaa Xaa Xaa Pro Xaa
1               5
```

(2) INFORMATION FOR SEQ ID NO: 148:

(i) SEQUENCE CHARACTERISTICS:
      (A) LENGTH: 9 amino acids
      (B) TYPE: amino acid
      (D) TOPOLOGY: linear (ix) FEATURE:
      (A) NAME/KEY: Modified-site
      (B) LOCATION: 1
      (D) OTHER INFORMATION: /note= "Xaa at position 1
         represents Ser or Thr"

(ix) FEATURE:
      (A) NAME/KEY: Modified-site
      (B) LOCATION: 2
      (D) OTHER INFORMATION: /note= "Xaa at position 2
         represents Lys, Arg, Homoarg or Orn"

(ix) FEATURE:
      (A) NAME/KEY: Modified-site
      (B) LOCATION: 4
      (D) OTHER INFORMATION: /note= "Xaa at position 4
         represents Ala or Gly"

(ix) FEATURE:
      (A) NAME/KEY: Modified-site
      (B) LOCATION: 5
      (D) OTHER INFORMATION: /note= "Xaa at position 5
         represents Ala or Gly"

(ix) FEATURE:
      (A) NAME/KEY: Modified-site
      (B) LOCATION: 6
      (D) OTHER INFORMATION: /note= "Xaa at position 6
         represents Lys, Arg, Homoarg or Orn"

(ix) FEATURE:
      (A) NAME/KEY: Modified-site
      (B) LOCATION: 7
      (D) OTHER INFORMATION: /note= "Xaa at position 7
         represents Leu, Ile, Val, Met or Norleu"

(ix) FEATURE:
      (A) NAME/KEY: Modified-site
      (B) LOCATION: 8
      (D) OTHER INFORMATION: /note= "Xaa at position 8
         represents Ser or Thr"

(ix) FEATURE:
      (A) NAME/KEY: Modified-site
      (B) LOCATION: 9
      (D) OTHER INFORMATION: /note= "Xaa at position 9
         represents Lys, Arg, Homoarg or Orn"

(xi) SEQUENCE DESCRIPTION: SEQ ID NO: 148:

Xaa Xaa Pro Xaa Xaa Xaa Xaa Xaa Xaa
1             5

(2) INFORMATION FOR SEQ ID NO: 149:

(i) SEQUENCE CHARACTERISTICS:
      (A) LENGTH: 8 amino acids
      (B) TYPE: amino acid
      (D) TOPOLOGY: linear (ix) FEATURE:
      (A) NAME/KEY: Modified-site
      (B) LOCATION: 1
      (D) OTHER INFORMATION: /note= "Xaa at position 1
         represents Lys, Arg, Homoarg or Orn"

```
    (ix) FEATURE:
         (A) NAME/KEY: Modified-site
         (B) LOCATION: 2
         (D) OTHER INFORMATION: /note= "Xaa at position 2
             represents Ala or Gly"

(ix) FEATURE:
         (A) NAME/KEY: Modified-site
         (B) LOCATION: 3
         (D) OTHER INFORMATION: /note= "Xaa at position 3
             represents Gln or Asn"

(ix) FEATURE:
         (A) NAME/KEY: Modified-site
         (B) LOCATION: 4
         (D) OTHER INFORMATION: /note= "Xaa at position 4
             represents Ser or Thr"

(ix) FEATURE:
         (A) NAME/KEY: Modified-site
         (B) LOCATION: 5
         (D) OTHER INFORMATION: /note= "Xaa at position 5
             represents Leu, Ile, Val, Met or Norleu"

(ix) FEATURE:
         (A) NAME/KEY: Modified-site
         (B) LOCATION: 6
         (D) OTHER INFORMATION: /note= "Xaa at position 6
             represents Ser or Thr"

(ix) FEATURE:
         (A) NAME/KEY: Modified-site
         (B) LOCATION: 8
         (D) OTHER INFORMATION: /note= "Xaa at position 8
             represents Ala or Gly"

(xi) SEQUENCE DESCRIPTION: SEQ ID NO: 149:

Xaa Xaa Xaa Xaa Xaa Xaa Pro Xaa
1               5

(2) INFORMATION FOR SEQ ID NO: 150:

(i) SEQUENCE CHARACTERISTICS:
         (A) LENGTH: 9 amino acids
         (B) TYPE: amino acid
         (D) TOPOLOGY: linear (ix) FEATURE:
         (A) NAME/KEY: Modified-site
         (B) LOCATION: 1
         (D) OTHER INFORMATION: /note= "Xaa at position 1
             represents Leu, Ile, Val, Met or Norleu"

(ix) FEATURE:
         (A) NAME/KEY: Modified-site
         (B) LOCATION: 3
         (D) OTHER INFORMATION: /note= "Xaa at position 3
             represents Ala or Gly"

(ix) FEATURE:
         (A) NAME/KEY: Modified-site
         (B) LOCATION: 4
         (D) OTHER INFORMATION: /note= "Xaa at position 4
             represents Lys, Arg, Homoarg, or Orn"

(ix) FEATURE:
         (A) NAME/KEY: Modified-site
         (B) LOCATION: 5
         (D) OTHER INFORMATION: /note= "Xaa at position 5
             represents Glu or Asp"

(ix) FEATURE:
         (A) NAME/KEY: Modified-site
         (B) LOCATION: 6
         (D) OTHER INFORMATION: /note= "Xaa at position 6
             represents Leu, Ile, Val, Met or Norleu"
```

```
    (ix) FEATURE:
         (A) NAME/KEY: Modified-site
         (B) LOCATION: 7
         (D) OTHER INFORMATION: /note= "Xaa at position 7
             represents Leu, Ile, Val, Met or Norleu"

(ix) FEATURE:
         (A) NAME/KEY: Modified-site
         (B) LOCATION: 8
         (D) OTHER INFORMATION: /note= "Xaa at position 8
             represents Lys, Arg, Homoarg or Orn"

(ix) FEATURE:
         (A) NAME/KEY: Modified-site
         (B) LOCATION: 9
         (D) OTHER INFORMATION: /note= "Xaa at position 9
             represents Ala or Gly"

(xi) SEQUENCE DESCRIPTION: SEQ ID NO: 150:

Xaa Pro Xaa Xaa Xaa Xaa Xaa Xaa Xaa
1               5

(2) INFORMATION FOR SEQ ID NO: 151:

(i) SEQUENCE CHARACTERISTICS:
        (A) LENGTH: 10 amino acids
        (B) TYPE: amino acid
        (D) TOPOLOGY: linear (ix) FEATURE:
         (A) NAME/KEY: Modified-site
         (B) LOCATION: 1
         (D) OTHER INFORMATION: /note= "Xaa at position 1
             represents Lys, Arg, Homoarg or Orn"

(ix) FEATURE:
         (A) NAME/KEY: Modified-site
         (B) LOCATION: 2
         (D) OTHER INFORMATION: /note= "Xaa at position 2
             represents Lys, Arg, Homoarg or Orn"

(ix) FEATURE:
         (A) NAME/KEY: Modified-site
         (B) LOCATION: 3
         (D) OTHER INFORMATION: /note= "Xaa at position 3
             represents Ser or Thr"

(ix) FEATURE:
         (A) NAME/KEY: Modified-site
         (B) LOCATION: 5
         (D) OTHER INFORMATION: /note= "Xaa at position 5
             represents Gln or Asn"

(ix) FEATURE:
         (A) NAME/KEY: Modified-site
         (B) LOCATION: 6
         (D) OTHER INFORMATION: /note= "Xaa at position 6
             represents Glu or Asp"

(ix) FEATURE:
         (A) NAME/KEY: Modified-site
         (B) LOCATION: 7
         (D) OTHER INFORMATION: /note= "Xaa at position 7
             represents Leu, Ile, Val, Met or Norleu"

(ix) FEATURE:
         (A) NAME/KEY: Modified-site
         (B) LOCATION: 8
         (D) OTHER INFORMATION: /note= "Xaa at position 8
             represents Leu, Ile, Val, Met or Norleu"

(ix) FEATURE:
         (A) NAME/KEY: Modified-site
         (B) LOCATION: 10
         (D) OTHER INFORMATION: /note= "Xaa at position 10
             represents Ala or Gly"
```

(xi) SEQUENCE DESCRIPTION: SEQ ID NO: 151:

Xaa Xaa Xaa Pro Xaa Xaa Xaa Xaa Pro Xaa
1               5                   10

(2) INFORMATION FOR SEQ ID NO: 152:

(i) SEQUENCE CHARACTERISTICS:
       (A) LENGTH: 7 amino acids
       (B) TYPE: amino acid
       (D) TOPOLOGY: linear (ix) FEATURE:
       (A) NAME/KEY: Modified-site
       (B) LOCATION: 1
       (D) OTHER INFORMATION: /note= "Xaa at position 1
           represents Leu, Ile, Val, Met or Norleu"

(ix) FEATURE:
       (A) NAME/KEY: Modified-site
       (B) LOCATION: 3
       (D) OTHER INFORMATION: /note= "Xaa at position 3
           represents Gln or Asn"

(ix) FEATURE:
       (A) NAME/KEY: Modified-site
       (B) LOCATION: 4
       (D) OTHER INFORMATION: /note= "Xaa at position 4
           represents Glu or Asp"

(ix) FEATURE:
       (A) NAME/KEY: Modified-site
       (B) LOCATION: 5
       (D) OTHER INFORMATION: /note= "Xaa at position 5
           represents Glu or Asp"

(ix) FEATURE:
       (A) NAME/KEY: Modified-site
       (B) LOCATION: 6
       (D) OTHER INFORMATION: /note= "Xaa at position 6
           represents Gln or Asn"

(ix) FEATURE:
       (A) NAME/KEY: Modified-site
       (B) LOCATION: 7
       (D) OTHER INFORMATION: /note= "Xaa at position 7
           represents Glu or Asp"

(xi) SEQUENCE DESCRIPTION: SEQ ID NO: 152:

Xaa Pro Xaa Xaa Xaa Xaa Xaa
1               5

(2) INFORMATION FOR SEQ ID NO: 153:

(i) SEQUENCE CHARACTERISTICS:
       (A) LENGTH: 10 amino acids
       (B) TYPE: amino acid
       (D) TOPOLOGY: linear (ix) FEATURE:
       (A) NAME/KEY: Modified-site
       (B) LOCATION: 1
       (D) OTHER INFORMATION: /note= "Xaa at position 1
           represents Ala or Gly"

(ix) FEATURE:
       (A) NAME/KEY: Modified-site
       (B) LOCATION: 3
       (D) OTHER INFORMATION: /note= "Xaa at position 3
           represents Tyr, Phe or Trp"

(ix) FEATURE:
       (A) NAME/KEY: Modified-site
       (B) LOCATION: 4
       (D) OTHER INFORMATION: /note= "Xaa at position 4
           represents Gln or Asn"

```
(ix) FEATURE:
    (A) NAME/KEY: Modified-site
    (B) LOCATION: 5..9
    (D) OTHER INFORMATION: /note= "Xaa at positions 5-9
        represent Leu, Ile, Val, Met or Norleu"

(ix) FEATURE:
    (A) NAME/KEY: Modified-site
    (B) LOCATION: 10
    (D) OTHER INFORMATION: /note= "Xaa at position 10
        represents Gln or Asn"

(xi) SEQUENCE DESCRIPTION: SEQ ID NO: 153:

Xaa Pro Xaa Xaa Xaa Xaa Xaa Xaa Xaa Xaa
1               5                   10
```